United States Patent
Eilers et al.

(10) Patent No.: US 8,496,588 B2
(45) Date of Patent: Jul. 30, 2013

(54) PROCEDURES FOR AN ULTRASONIC ARC SCANNING APPARATUS

(75) Inventors: George J. Eilers, Evergreen, CO (US);
J. David Stienmier, Denver, CO (US);
Wes Weber, Golden, CO (US); Eric Osmann, Evergreen, CO (US); Randy Rasmussen, Minneapolis, MN (US);
Paul McGregor, Evergreen, CO (US);
Olga Medvedeva, Golden, CO (US)

(73) Assignee: Arcscan, Inc., Golden, CO (US)

( * ) Notice: Subject to any disclaimer, the term of this patent is extended or adjusted under 35 U.S.C. 154(b) by 724 days.

(21) Appl. No.: 12/418,392

(22) Filed: Apr. 3, 2009

(65) Prior Publication Data
US 2010/0004537 A1 Jan. 7, 2010

Related U.S. Application Data

(60) Provisional application No. 61/042,170, filed on Apr. 3, 2008.

(51) Int. Cl.
*A61B 8/00* (2006.01)

(52) U.S. Cl.
USPC ........... 600/443; 600/407; 600/437; 600/452; 73/620

(58) Field of Classification Search
USPC .... 600/407, 437, 443, 444, 452, 459; 73/579, 73/619, 627, 634
See application file for complete search history.

(56) References Cited

U.S. PATENT DOCUMENTS

| | | | |
|---|---|---|---|
| 3,371,660 A | 3/1968 | Benson | |
| 3,821,891 A | 7/1974 | Collins et al. | |
| 4,114,214 A | 9/1978 | VonHeck | |
| 4,183,249 A * | 1/1980 | Anderson | 73/626 |
| 4,206,763 A | 6/1980 | Pedersen | |
| 4,227,780 A | 10/1980 | Ohta et al. | |
| 4,245,250 A | 1/1981 | Tiemann | |
| 4,347,213 A | 8/1982 | Rogers | |
| 4,484,569 A * | 11/1984 | Driller et al. | 600/439 |
| 4,550,607 A | 11/1985 | Maslak et al. | |
| 4,564,018 A | 1/1986 | Hutchison et al. | |
| 4,807,634 A | 2/1989 | Enjoji et al. | |
| 4,815,047 A | 3/1989 | Hart | |
| 4,817,432 A * | 4/1989 | Wallace et al. | 73/602 |
| 4,823,801 A | 4/1989 | Sakane | |

(Continued)

FOREIGN PATENT DOCUMENTS

| | | |
|---|---|---|
| CA | 2295431 | 7/2001 |
| CA | 2299483 | 7/2001 |

(Continued)

OTHER PUBLICATIONS

International Preliminary Report on Patentability for International Application No. PCT/US2009/039505, mailed Oct. 14, 2010.

(Continued)

*Primary Examiner* — Unsu Jung
*Assistant Examiner* — Michael N Fisher
(74) *Attorney, Agent, or Firm* — Sheridan Ross PC

(57) ABSTRACT

Embodiments of the present invention are directed to methods of rapidly obtaining ultrasonic images of the eye using a set of procedural options that can be automated by a positioning mechanism that can be controlled by software.

21 Claims, 12 Drawing Sheets

U.S. PATENT DOCUMENTS

| | | | |
|---|---|---|---|
| 4,858,124 A * | 8/1989 | Lizzi et al. | 600/443 |
| 4,858,613 A | 8/1989 | Fry et al. | |
| 4,930,512 A * | 6/1990 | Henriksen et al. | 600/452 |
| 4,932,414 A | 6/1990 | Coleman et al. | |
| 5,029,587 A | 7/1991 | Baba et al. | |
| 5,079,786 A | 1/1992 | Rojas | |
| 5,103,517 A | 4/1992 | Krouskop | |
| 5,116,114 A * | 5/1992 | Nakamura et al. | 351/205 |
| 5,293,871 A | 3/1994 | Reinstein et al. | |
| 5,331,962 A * | 7/1994 | Coleman et al. | 600/444 |
| 5,369,454 A | 11/1994 | Reinstein et al. | |
| 5,387,180 A | 2/1995 | Lehmer | |
| 5,460,179 A | 10/1995 | Okunuki et al. | |
| 5,487,388 A | 1/1996 | Rello et al. | |
| 5,556,169 A | 9/1996 | Parrish et al. | |
| 5,614,099 A | 3/1997 | Hirose et al. | |
| 5,626,150 A | 5/1997 | Johnson et al. | |
| 5,626,594 A | 5/1997 | Smith | |
| 5,776,068 A * | 7/1998 | Silverman et al. | 600/443 |
| 5,826,583 A | 10/1998 | Wood | |
| 5,832,550 A | 11/1998 | Hauger et al. | |
| 5,855,207 A | 1/1999 | Moenning et al. | |
| 5,906,205 A | 5/1999 | Hiebert | |
| 5,966,763 A | 10/1999 | Thomas et al. | |
| 5,971,006 A | 10/1999 | Seigerschmidt | |
| 6,053,613 A | 4/2000 | Wei et al. | |
| 6,145,143 A | 11/2000 | Hicks et al. | |
| 6,154,204 A * | 11/2000 | Thompson et al. | 375/214 |
| 6,198,956 B1 | 3/2001 | Dunne | |
| 6,315,727 B1 | 11/2001 | Coleman et al. | |
| 6,374,439 B2 | 4/2002 | Heimbrock et al. | |
| 6,487,447 B1 | 11/2002 | Weimann et al. | |
| 6,491,637 B2 | 12/2002 | Foster et al. | |
| 6,574,813 B2 | 6/2003 | Bolden et al. | |
| 6,629,929 B1 * | 10/2003 | Jago et al. | 600/447 |
| 6,837,855 B1 | 1/2005 | Puech | |
| 6,868,569 B2 | 3/2005 | VanSteenburg | |
| 6,887,203 B2 | 5/2005 | Phillips et al. | |
| 6,923,767 B2 | 8/2005 | Saied et al. | |
| 6,981,417 B1 * | 1/2006 | Oravecz | 73/619 |
| 7,048,690 B2 * | 5/2006 | Coleman et al. | 600/452 |
| 7,168,116 B2 | 1/2007 | Reger et al. | |
| 7,356,905 B2 | 4/2008 | Ketterling et al. | |
| 7,454,024 B2 | 11/2008 | Ketterling et al. | |
| 7,474,041 B2 | 1/2009 | Ketterling et al. | |
| 2003/0004416 A1 * | 1/2003 | Phillips et al. | 600/459 |
| 2003/0142269 A1 | 7/2003 | Cumming | |
| 2004/0220478 A1 | 11/2004 | Wallace et al. | |
| 2005/0120479 A1 | 6/2005 | Habashi et al. | |
| 2006/0029525 A1 * | 2/2006 | Laugharn et al. | 422/130 |
| 2006/0241533 A1 | 10/2006 | Geller | |
| 2007/0083995 A1 | 4/2007 | Purdy et al. | |
| 2007/0239030 A1 | 10/2007 | Prager et al. | |
| 2007/0276233 A1 | 11/2007 | Besson et al. | |
| 2008/0097214 A1 | 4/2008 | Meyers et al. | |
| 2009/0234369 A1 | 9/2009 | Bax et al. | |
| 2010/0031448 A1 | 2/2010 | Hijlkema | |

FOREIGN PATENT DOCUMENTS

| | | |
|---|---|---|
| CA | 2395203 | 7/2001 |
| CA | 2409234 | 4/2004 |
| JP | 2006-149001 | 6/2006 |

OTHER PUBLICATIONS

International Preliminary Report on Patentability for International Application No. PCT/US2009/088671, mailed Jul. 15, 2010.
Extended Search Report for European Patent Application No. 08870422.6, dated May 31, 2011 9 pages.
Official Action for European Patent Application No. 08870422.6, date Jun. 17, 2011 1 page.
Official Action for U.S. Appl. No. 12/347,674, mailed Oct. 27, 2011 9 pages Restriction Requirement.
Official Action for U.S. Appl. No. 12/347,674, mailed Mar. 2, 2012 10 pages.
U.S. Appl. No. 12/638,661, filed Dec. 15, 2009, Eilers et al.
U.S. Appl. No. 12/754,444, filed Apr. 5, 2010, Eilers et al.
Official Action for U.S. Appl. No. 12/347,674, mailed Aug. 14, 2012 10 pages.
U.S. Appl. No. 13/684,699, filed Nov. 26, 2012, Watson.
Binder, "SL-OCT and Ultrasound Support the Need for New Phakic IOL Sizing Strategies", Euro Times, p. 11, Mar. 2007.
Coleman et al., "Ultrasonography of the Eye and Orbit", Second Edition, published by Lippincott Williams & Wilkins, pp. 1-186, 2006.
U.S. Appl. No. 12/475,322, filed May 29, 2009, Eilers et al.
U.S. Appl. No. 12/347,674, filed Dec. 31, 2008, Eilers et al.
Ketterling, "Design and Fabrication of a 40-MHz Annular Array Transducer", IEEE Transactions on Ultrasonics, Ferroelectrics, and Frequency Control, pp. 672-681, vol. 52, No. 4, Apr. 2005.
Ketterling, "Operational Verification of a 40-MHz Annular Array Transducer", IEEE Transactions on Ultrasonics, Ferroelectrics, and Frequency Control, pp. 623-630, vol. 53, No. 3, Mar. 2006.
Mamou, "Chirp-Coded Excitation Imaging With a High-Frequency Ultrasound Annular Array", IEEE Transactions on Ultrasonics, Ferroelectrics, and Frequency Control, vol. 55, No. 2, Feb. 2008.
Pinero et al., "Equivalence, Differences Identified in Biometric Analysis", Cataract & Refractive Surgery Today, vol. 3, No. 12, pp. 46-49, Mar. 2008.
Reinstein, "Subsurface Screening for Keratoconus—Accurate Measurements of the Epithelial and Stromal Layers Aid in Diagnosis", Cataract and Refractive Surgery Today, pp. 88-89, May 2007.
Roholt, "Sizing the Visian ICL", Cataract and Refractive Surgery Today, p. 50, May 2007.
Silverman et al., "Improved System for Sonographic Imaging and Biometry of the Cornea", pp. 117-124, 1997, Imaging and Biometry of Cornea, J. Ultrasound Med. 16:117-124.
International Search Report for International Application No. PCT/US2008/088671, mailed May 8, 2009.
Written Opinion for International Application No. PCT/US2009/088671, mailed May 8, 2009.
International Search Report for International Application No. PCT/US2009/039505, mailed Jun. 3, 2009.
Written Opinion for International Application No. PCT/US2009/039505, mailed Jun. 3, 2009.
Background of the Invention for the above-captioned application (previously provided).

* cited by examiner

PROCEDURES FOR AN ULTRASONIC ARC SCANNING APPARATUS

CROSS REFERENCE TO RELATED APPLICATION

The present application claims the benefits, under 35 U.S.C. §119(e), of U.S. Provisional Application Serial No. 61/042,170 entitled "Innovative Components and Procedures for an Ultrasonic Arc Scanning Apparatus", filed Apr. 3, 2008, which is incorporated herein by this reference.

FIELD

The present invention relates to ultrasonic imaging of biological materials such as the cornea and the lens of the eye and in particular relates to innovative methods for obtaining accurate images with an ultrasonic arc scanning apparatus, such as a range finding and centering algorithms for aligning the scanning apparatus.

BACKGROUND

Ultrasonic imaging has found use in accurate measurement of structures of the eye, such as, for example, the cornea. Such measurements provide an ophthalmic surgeon valuable information that he can use to guide various surgical procedures performed on the cornea, one of the principal ones being the LASIK procedure for correcting refractive errors. They also provide diagnostic information after surgery has been performed to assess the geometrical location of corneal features such as the LASIK scar. This allows the surgeon to assess post surgical changes in the cornea as the cornea heals and to take steps to correct problems that can develop.

Ultrasonic imaging of the cornea presents a problem not generally encountered in other types of tissue. The corneal surfaces are necessarily smooth and spherically shaped to perform the optical function of focusing light rays. Because the corneal structures are smooth and regular, ultrasonic energy is reflected only in specific directions. In particular, an ultrasound beam from a transducer will only be reflected directly back to that transducer when the beam is aligned perpendicular to the corneal surface. This kind of reflective property is called specular reflection.

Because of the specular property of corneal surfaces, it will be appreciated that special care must be taken to align the transducer with the cornea at each position from which a partial image is to be formed. Ultrasonic imaging of large portions of the cornea can be accomplished by scanning the transducer along the cornea surface while continually adjusting the alignment of the transducer to provide a beam that is always directed toward the cornea's center of curvature.

Corneal imaging and measuring of corneal dimensions require that the scanning motion of the transducer be smooth and precisely aligned. Departures, even as small as 5 microns, of the transducer position from a circular path or of the beam's direction from the center of curvature can significantly degrade the resulting image. Mechanisms for performing the requisite scan alignment are described in U.S. Pat. Nos. 6,491,637 and 5,331,962 which are incorporated herein by reference. The reference "Ultrasonography of the Eye and Orbit", Second Edition, Coleman et al, published by Lippincott Williams & Wilkins, 2006 contains an excellent historical and technical summary of ultrasonic imaging of the eye and is incorporated herein by this reference.

While ultrasonic imaging may be used by ophthalmologists for quantitative analysis of laser refractive surgery, it may also be used for implantation of corneal and phakic lenses, implantation of intraocular lenses and specialty procedures such as glaucoma and cataract treatment.

Except for on-axis measurements, dimensions of eye components behind the iris cannot be determined by optical means. New procedures such as implantation of accommodative lenses may provide nearly perfect vision without spectacles or contact lenses. Implantation of accommodative lenses requires precision measurements of, for example, the lens width for successful lens implantation. Ultrasonic imaging can be used to provide the required accurate images of the lens and its associated zonules especially where it attaches to the ciliary muscle which is well off-axis and behind the iris and therefore not accessible to optical imaging.

Conventional ultrasonic scanning techniques and algorithms are currently limited in that most require expert users to manually move some of the elements of the scan head positioning apparatus for alignment which requires the patient to remain longer with their eye immersed in water. This can result in substandard images due to patient movement, especially of the eye blinking during a scan procedure.

There remains, therefore, a need for ultrasonic scanner mechanisms and procedures that will enable rapid and often complex imaging sequences that can be completed before the patient becomes uncomfortable.

SUMMARY

These and other needs are addressed by the present invention. The various embodiments and configurations of the present invention are directed generally to ultrasonic imaging of biological materials such as the cornea and lens of the eye and in particular directed to methods of rapidly obtaining ultrasonic images of the eye using a set of procedural options that can be automated by a positioning mechanism that can be controlled by software.

Several of the complex procedures described herein may be automated because of the use of a compact scan head positioning mechanism whose motions can be scripted and executed under software control. An acoustic transducer carriage is typically guided by a guide configured as a track, so that the transducer beam axis is continuously directed towards a fixed center point regardless of the transducer carriage's position along the guide. The guide assembly is typically formed in the fixed shape of an arc that approximates the curvature of the eye's cornea or anterior lens surface. The scan head positioning mechanism allows the scanning head guide assembly to: be moved back and forth axially (the z-direction) for focusing; be rotated about its z-axis (the beta-direction) for selection of a scan meridian; be moved up and down (the y-direction); and be moved from side to side (the x-direction) for centering. These motions may be executed under computer control by use of suitable positioning mechanisms.

In one embodiment, an ocular imaging method is disclosed, comprising: receiving, from an operator, a selection of at least one feature of a patient's eye, a set of scan meridians comprising a prime scan meridian and one or more secondary scan meridians, and a set of scan analysis instructions; receiving, from an operator, a selection of an approximate center location of an ultrasonic transducer relative to at least one selected feature of the patient's eye; determining, by a processor, a first approximate range of an ultrasonic transducer aperture respecting the at least one selected feature of the patient's eye; altering a position at least one of an ultrasonic transducer and arcuate guide relative to the at least one selected feature of the patient's eye; determining, by a processor, a predetermined range of the at least one of an ultrasonic transducer and arcuate guide respecting the at least one selected feature of the patient's eye; executing, based on the set of scan meridians, a series of ultrasonic scans of the patient's eye; and executing, based on the set of scan analysis instructions, at least one of a set of acoustic images for each selected scan meridian, a set of eye component thickness maps, and major dimensions of the selected eye components.

In another embodiment, an ocular imaging system is disclosed, comprising: an ultrasound transducer; an arcuate guide for the ultrasound transducer; a plurality of positional displacement devices to displace the arcuate guide and the transducer to a selected position and orientation; an input operable to receive, from an operator, at least one of a selection of at least one feature of a patient's eye, a set of scan meridians comprising a prime scan meridian and a plurality of secondary scan meridians, and a set of scan analysis instructions; and a processor operable to perform the following operations: determine a first range of an ultrasonic transducer aperture respecting the selected feature of the patient's eye; center the ultrasonic transducer and arcuate guide relative to the selected feature of the patient's eye; determine a predetermined range of the ultrasonic transducer aperture respecting the selected feature of the patient's eye; execute, based on the set of scan meridians, a series of ultrasonic scans of the patient's eye; and execute, based on the set of scan analysis instructions, at least one of a set of acoustic images for each selected scan meridian, a set of eye component thickness maps, and major dimensions of the selected eye components.

The following definitions are used herein:

An A-scan is a representation of the reflected acoustic signal amplitudes as a function of time received by an ultrasonic transducer from acoustic pulses originally emitted by the ultrasonic transducer from a known fixed position relative to an eye component.

An accommodative lens, also known as a presbyopic lens or presby lens, is an artificial intraocular lens that changes its focal distance in response to contraction of the ciliary muscle. When successfully implanted, an accommodative lens reverses presbyopia, the inability of the eye to change its focal distance from far to near.

Aligning means positioning the transducer and transducer carriage guide preferably accurately and reproducibly in space with respect to a feature of the eye component of interest (such as the center of curvature or boundary of the cornea, lens, retina, etcetera).

The anterior chamber comprises the region of the eye from the front of the eye to the iris.

The anterior segment comprises the region of the eye from the front of the eye to just beyond the back of the lens.

An aperture refers to the ultrasonic transducer face which may be planar but is commonly shaped as a concave surface so as to form a focal point at a desired location.

An arc scanner is a scanning device where the sensor moves in a substantially precise arc about the center of the area to be scanned with its beam constantly directed through a central point.

Arc scanning transducer center of curvature is the same as the center of curvature of the arc scanning guide.

Auto-centering means automatically, typically under computer control, causing centration of the arc scanning transducer with the eye component of interest.

A B-scan is processed representation of A-scan data by either or both of converting it from a time to a distance using acoustic velocities or by using grayscales which correspond to A-scan amplitudes highlight the features along the A-scan time history trace (also referred to as an A-scan vector).

A canthus is the angular junction of the eyelids at either corner of the eye where the upper and lower eyelids meet.

Centration means substantially aligning the center of curvature of the arc scanning transducer in space with the center of curvature of the eye component of interest (such as the cornea, lens, retina, etcetera) such that rays from the transducer pass through both centers of curvature. A special case is when both centers of curvature are coincident.

The ciliary body is the circumferential tissue inside the eye composed of the ciliary muscle and ciliary processes. There are three sets of ciliary muscles in the eye, the longitudinal, radial, and circular muscles. They are near the front of the eye, above and below the lens. They are attached to the lens by connective tissue called the zonule of Zinn, and are responsible for shaping the lens to focus light on the retina. When the ciliary muscle relaxes, it flattens the lens, generally improving the focus for farther objects. When it contracts, the lens becomes more convex, generally improving the focus for closer objects.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

A guide is an apparatus for directing the motion of another apparatus.

Haptics are little curved hair-like protrusions extending from the outer diameter of some types of artificial lenses. These haptics attach these lens to the ciliary muscle by protruding into the ciliary sulcus and allow the lens to accommodate in response to the action of the ciliary muscle.

An intraocular lens is an artificial lens that is implanted in the eye to take the place of the natural lens.

LASIK is a procedure performed on the cornea for correcting refractive errors, such as myopia, hyperopia, and astigmatism. Commonly, an excimer laser selectively removes tissue from the inside of the cornea, after exposing it by cutting a thin flap, so as to reshape the external shape of the cornea.

A meridian is a plane that cuts through a portion of a three-dimensional component such as the cornea or natural lens of the eye and its angle is commonly expressed relative to a horizon defined by the canthi.

The natural lens (also known as the aquula or crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: namely the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are generally found only on the anterior side of the lens.

Ocular means having to do with the eye or eyeball.

Ophthalmology means the branch of medicine that deals with the eye.

Optical as used herein refers to processes that use light rays.

The optical axis of the eye is the line of best fit joining the centers of curvature of the refracting surfaces (the anterior and posterior surfaces of the cornea and lens).

Pachymetry or corneal pachymetry is technically referred to as Time Domain Reflectometry ultrasound. A pulse of ultrasonic energy is sent toward the cornea and the time spacing of the returning echoes are used to arrive at corneal thickness.

Phakic intraocular lenses, or phakic lenses, are lenses made of plastic or silicone that are implanted into the eye permanently to reduce a person's need for glasses or contact lenses. Phakic refers to the fact that the lens is implanted into the eye without removing the eye's natural lens. During phakic lens implantation surgery, a small incision is normally made in the front of the eye. The phakic lens is inserted through the incision and placed just in front of or just behind the iris.

The posterior chamber comprises the region of the eye from the back of the iris to the front of the lens.

The posterior segment comprises the region of the eye from the back of the lens to the rear of the eye comprising the retina and optical nerve.

Presbyiopia is typically caused by a loss of elasticity of the natural lens inside the eye. This occurs as part of the ageing process and, although it cannot be 'cured', it can be corrected by wearing glasses or implanting an artificial lens.

Purkinje images are reflections of objects from structure of the eye. There are at least four Purkinje images that are visible on looking at an eye. The first Purkinje image (P1) is the reflection from the outer surface of the cornea. The second Purkinje image (P2) is the reflection from the inner surface of the cornea. The third Purkinje image (P3) is the reflection from the outer (anterior) surface of the lens. The fourth Purkinje image (P4) is the reflection from the inner (posterior) surface of the lens. Unlike the others, P4 is an inverted image. The first and fourth Purkinje images are used by some eye trackers, devices to measure the position of an eye. Purkinje images are named after Czech anatomist Jan Evangelista Purkyne (1787-1869).

Refractive means anything pertaining to the focusing of light rays by the various components of the eye.

Registration means aligning.

Sector scanner is an ultrasonic scanner that sweeps out a sector like a radar. The swept area is pie-shaped with its central point typically located near the face of the ultrasound transducer.

A specular surface means a mirror-like surface that reflects either optical or acoustic waves. For example, an ultrasound beam emanating from a transducer will only be reflected directly back to that transducer when the beam is aligned perpendicular to a specular surface.

The ciliary sulcus is the groove between the iris and ciliary body. The scleral sulcus is a slight groove at the junction of the sclera and cornea.

A track is an apparatus along which another apparatus moves.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

A vector refers to a single acoustic pulse and its multiple reflections from various eye components. An A-scan is a representation of this data which is typically rectified.

The visual axis of the eye is the line joining the object of interest and the fovea and which passes through the nodal points.

Zonules are tension-able ligaments extending from near the outer diameter of the crystalline lens. The zonules attach the lens to the ciliary body which allows the lens to accommodate in response to the action of the ciliary muscle.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

DETAILED DESCRIPTION

Reference is made to U.S. patent application Ser. No. 12/347,674 filed Dec. 31, 2008 entitled "Components for an Ultrasonic Arc Scanning Apparatus" which describes many of the components of a modem arc scanning device and which is incorporated herein by reference. In an ultrasonic arc scanners, the transducer acts as both the transmitter and receiver of acoustic signals. The transducer emits a short acoustic pulse and then receives the reflected acoustic signal. The raw reflected signal, which is a voltage amplitude trace as a function of time, received by the transducer is commonly called an A-scan. This technique is described, for example, in U.S. Pat. No. 5,293,871 and in "Ultrasonography of the Eye and Orbit".

The procedures described herein provide a superior method for efficiently operating an arc scanner. These procedures may be automated because of the use of a compact scan head positioning mechanism whose motions can be scripted and executed under software control. Ab example of such a positioning mechanism is disclosed in U.S. patent application Ser. No. 12/347,674. The acoustic transducer carriage is typically guided by a guide, which is commonly configured as a track, so that the transducer beam axis is continuously directed towards a fixed center point regardless of the carriage's position along the guide. The embodiments described herein are illustrated by an arc scanner in which a scan head guide assembly is formed in the fixed shape of an arc that approximates the curvature of the eye's cornea or anterior lens surface. The scan head positioning mechanism allows the scanning head guide assembly to: be moved back and forth axially (the z-direction); be rotated about its z-axis (the beta-direction); be moved up and down (the y-direction); and be moved from side to side (the x-direction) by suitable mechanisms that are operated under computer control.

Ultrasonic Scanning Principles

Figure 1:
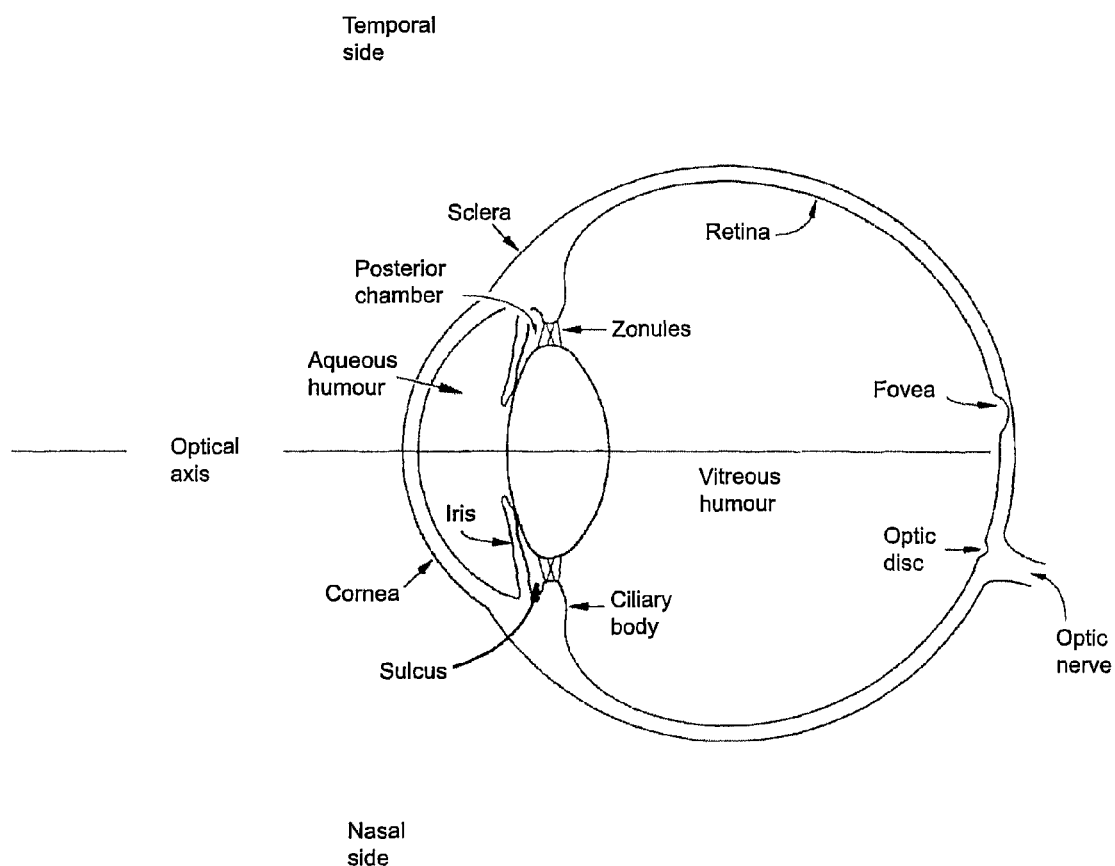
FIG. 1 is a schematic of the main elements of a human eye.

FIG. 1 is a schematic of the main elements of a human eye taken from U.S. patent application Ser. No. 12/347,674. The principal refracting components are the cornea, iris and lens. The cornea, which is optically transparent, is located at the front of the eye enclosing front of the anterior chamber. The iris separates the anterior chamber from the posterior chamber. The front of the lens encloses the back side of the posterior chamber. The natural lens sits directly behind the iris. Only the central part of the lens, which is behind the pupil, can be seen optically The anterior and posterior chambers comprise the anterior segment of the eye. The main volume or posterior segment of the eye lies behind the lens, with the retina and optical nerve at the rear of the posterior segment of the eye. The composition of the eye's aqueous and vitreous humour are very close to that of water with a density of about 1,000 $kg/m^3$, and this allows the eye to be a very good medium for the transmission of acoustic energy.

Optical means are suitable for viewing the anterior chamber and for viewing along the entire central axis of the eye. However, optical means cannot be used to view the portions of the posterior chamber lying immediately behind the iris, which includes the suspensory ligaments (called zonules), ciliary sulci and ciliary body. However, the eye components that cannot be viewed optically, can be viewed with high-frequency acoustic energy. As is well-known, acoustic frequencies in the ultrasonic range of about 10 MHz to about 60 MHz can be used to provide very high resolution images of, for example, the cornea and the lens and even foreign bodies in the vitreous humour.

Acoustic images can be made by two different types of scanning devices. One, called a sector scanner, is a hand-held device which is held against the patient's cornea and oscillated about a fixed position so as to produce an image of a localized region of interest within the eye. With a second type of acoustic scanner, called an arc scanner, a patient sits with an eye sealed by a water-filled eyepiece which maintains the patient in a fixed location with respect to an arc track. In this type of scanner, an ultrasonic transducer is moved in along the arc whose center is set at a location of interest in the eye. This type of scanner can produce a more comprehensive image of an arc of the eye from which quantitative measurements can be made. In both the arc and sector ultrasonic scanners, the transducer acts as both the transmitter and receiver of acoustic signals. The transducer emits a short acoustic pulse and then receives the reflected acoustic signal.

Figure 2:
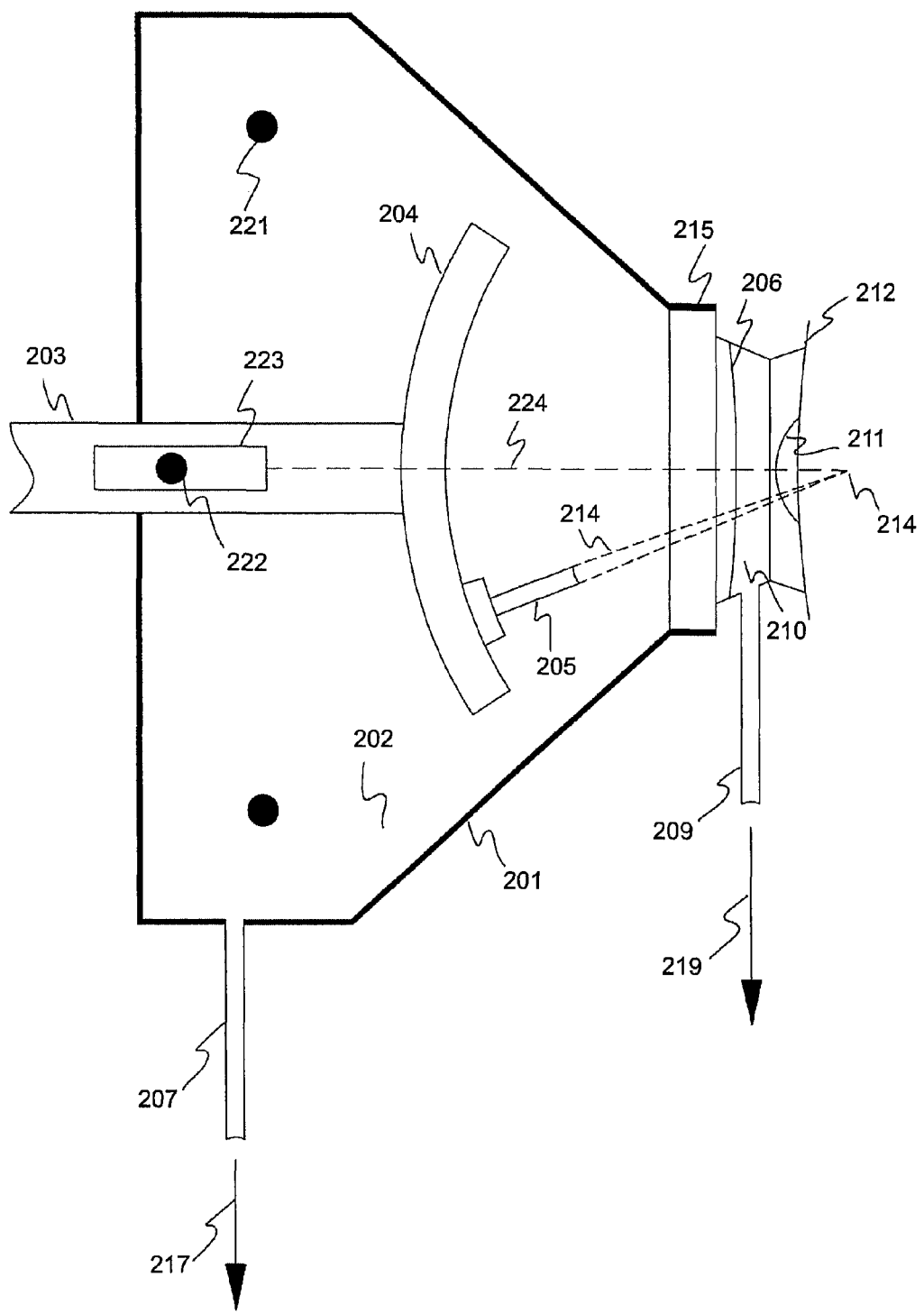
FIG. 2 is a schematic of a prior art arc scanning device.

FIG. 2 shows the main elements of a prior art arc scanning device illustrating positioning of a transducer along an arc guide whose center of curvature is centered approximately on the center of curvature of an eye component of interest. This figure was disclosed in U.S. patent application Ser. No. 12/347,674. FIG. 2 shows fixation lights 221 and 222 that allow the patient to fixate his or her eye to maintain it in a steady position during scanning. FIG. 2 also shows an optical video camera 223 which may be used by the operator of the arc scanner to monitor the position of the patient's eye and to determine whether the patient's eye is open before a scan is initiated. The transducer and its arc guide assembly are immersed in a chamber of water 202 to provide a continuous transmission path for the acoustic signals. The patient's eye must also be immersed in water to provide continuity of the transmission path for the acoustic signal. FIG. 2 also shows a hygienic barrier 206 which separates the water chamber 201 in which the transducer 205 and arc guide assembly 204 are contained from the water 210 in which the patients eye is immersed. This barrier 206 provides the separation of water 202 in which the transducer 205 and arc track assembly 204 are contained from the water 210 in which the patients eye is immersed. The arc guide assembly and associated components may be contaminated, for example, by particles from wearing mechanical components. The water 210 in which the patients eye is immersed may be contaminated by bacteria or virus particles from the patient. As can be appreciated, the water 210 in which the patients eye is immersed should be changed for every patient to prevent possible disease transmission. As can be further appreciated, the hygienic membrane 206 must be substantially transparent to ultrasound so as to maintain a clear acoustic transmission path between the patient's eye and the ultrasonic transducer. The hygienic membrane 206 is typically formed as part of a disposable eyepiece such as described in U.S. patent application Ser. No. 12/347,674.

FIG. 2 illustrates the continuity of an acoustic transmission path through water. A chamber 201 of water 202 is shown with a positioning arm 203 and arc guide assembly 204 on which an ultrasonic transducer 205 is mounted. A transparent barrier 206 separates chamber 201 from the interior of an eyepiece 208. The eyepiece 208 contains a separate volume of water 210 which fills the interior of the eyepiece 208 and contacts a patient's eye surface 211. The eyepiece 208 is connected and sealed to the main chamber 201 of the arc scanning device, and is also sealed against the patient's face 212. As can be seen, there is a continuous path through water from the transducer 205 to the patient's eye surface 211 for the efficient passage of acoustic energy. The barrier 206 readily passes acoustic energy without alteration, thus forming a portion of the continuous path between the transducer 205 and the patient's eye surface 211. Since the acoustic impedance of the patient's eye is approximately that of water, the acoustic energy from the transducer can be efficiently transmitted into the eye and reflected back from an eye component, such as for example, the surface of the cornea, to the transducer. Also shown in FIG. 2 are a water fill tube 207 for the main chamber 201 and a separate water fill tube 209 for the eyepiece 208. As can be appreciated, the water used in the eyepiece can be distilled or slightly saline to match the salinity of the eye, and the water used in the eyepiece can be introduced at a temperature that is comfortable for the patient.

Figure 3:
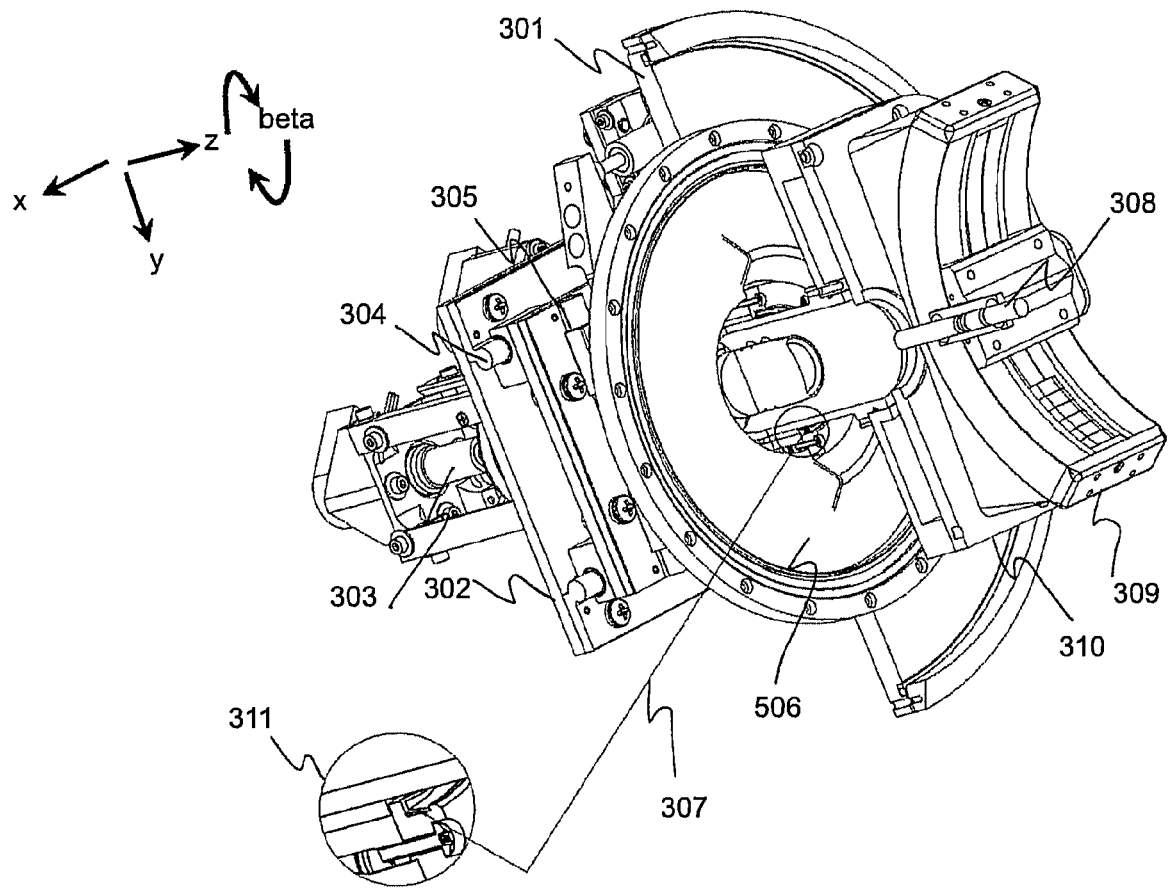
FIG. 3 illustrates a prior art compact arc scanning head positioning mechanism.

FIG. 3 further illustrates a compact scan head positioning mechanism and was disclosed in U.S. patent application Ser. No. 12/347,674. FIG. 3 shows an arc scanner head 309 with ultrasonic transducer 308 mounted on the end of a scanner head mount arm 310. These components (scanner head mount arm 310, scanner head 309 and ultrasonic transducer 308) are operative under water and are sealed from the rear portion of the positioning mechanism by a translational seal 306 and a rotational seal 307. The translational seal 306 is preferably formed by a large rubber membrane that can flex with the small x and y motions required by the scanning head positioner, though any sealing mechanism may be employed. The z-axis seal and rotational seal 307 are attached to a stationary plate 301 which is affixed to the main arc scanner assembly. The z-axis and rotational seal 307 is typically formed by a circumferential groove type sealing mechanism with the groove facing into the water, though any sealing mechanism may be employed. It allows both rotation and axial translation of the center tube while maintaining a water tight seal. The cross section of the seal is such that increased water pressure acts on the seal in a way that increases radial sealing force. The sealing surfaces are preferably anodized aluminum. Stationary plate 302 is also affixed to the main arc scanner assembly. The scanning head can be moved back and forth axially (the z-direction) by axial piston 303 or another suitable mechanism. The scanning head can be rotated (the beta-direction) about the z-axis by a rotary stepping motor (not shown) or another suitable device. The scanning head can be moved up and down (the y-direction) by piston 305 or another suitable mechanism. The scanning head can be moved from side to side (the x-direction) by piston 304 or another suitable mechanism. The components to the left or rear of stationary plate 301 remain in ambient air while the components to the right or font of stationary plate 301 are in immersed in water when the arc scanner is operational.

Figure 4:
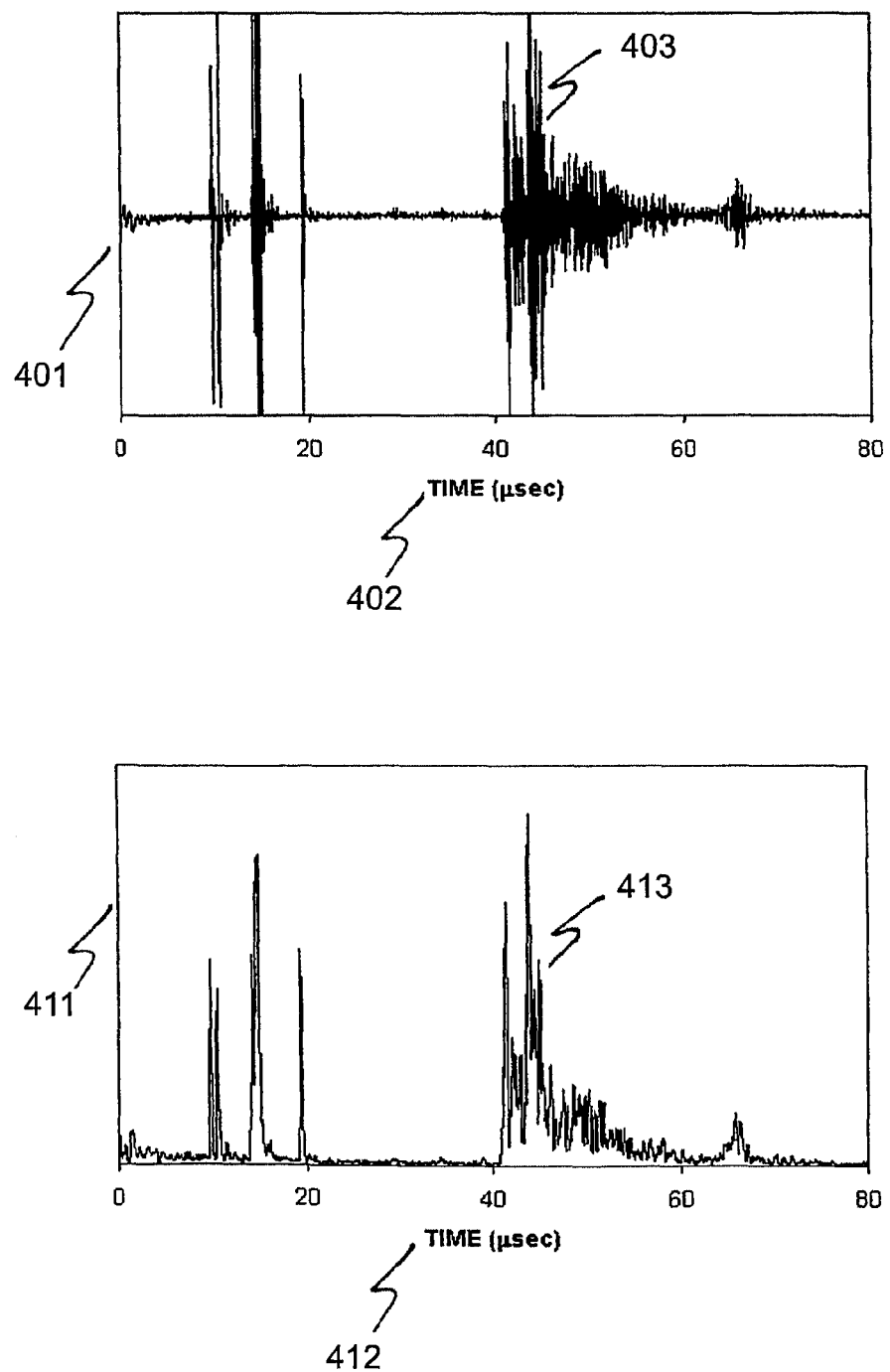
FIG. 4 illustrates an A-Scan which is prior art.

FIG. 4 illustrates a typical A-Scan and was taken from "Ultrasonography of the Eye and Orbit". An A-scan is the electronically recorded amplitude-time history of a reflected acoustic pulse received by the arc scanner's transducer. An raw A-scan 403 is shown as signal amplitude in volts 401 versus time 402 in microseconds. Typically an A-scan is displayed to the arc scanner operator as a rectified trace 413 with signal amplitude in volts 411 versus time 412 in microseconds. In addition to being rectified, the A-scan trace may also be filtered to remove unwanted thermal and electronic noise.

Figure 5:
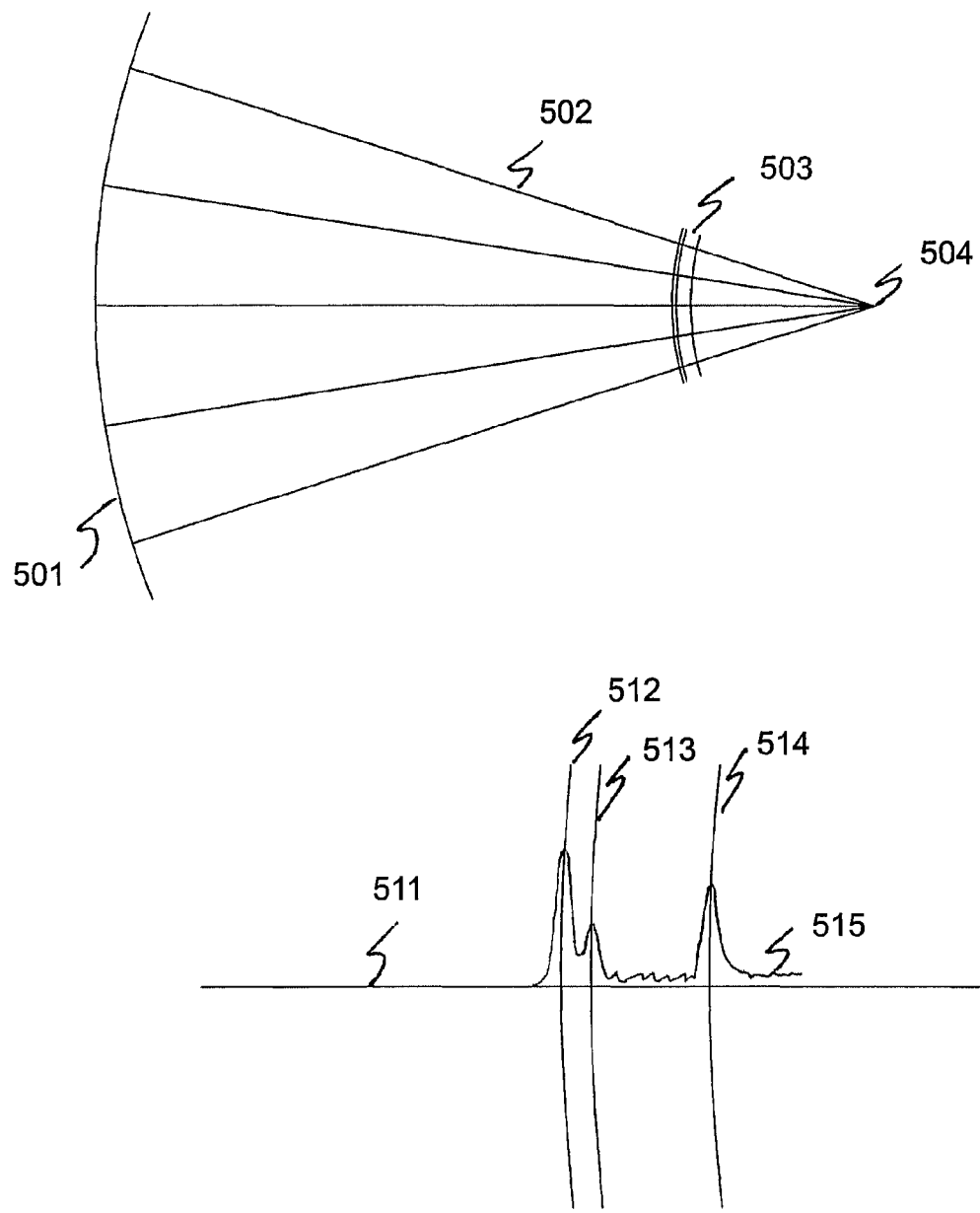
FIG. 5 illustrates the principle of a B-Scan which is prior art.

FIG. 5 illustrates the principle of a B-Scan for an arc scanning device. An arc path 501 for a transducer face is shown with several A-scan beam paths 502 traversing a cornea 503. The beam paths 502 all intersect at a center of curvature 504 of the arc path. The center of curvature 504 of the arc path is ideally set to coincide with the center of curvature of the cornea so that all beam paths are substantially normal to the surface of the cornea so that the amplitudes of the reflected acoustic signals are maximized. Emitted and reflected acoustic pulses along beam paths 502 each result in an A-scan. The time for a pulse to be emitted and its various reflections to be received by the transducer are very short compared to the time for the transducer carriage to move along the arc guide. In a modern arc scanning machine an A-scan is taken at incremental angles in the range of about 0.068 degrees to about 0.55 degrees. For example, 128 to 1,024 A-scans may be taken along an arc guide track with an included angle of 70 degrees. An A-scan is 515 is shown as amplitude along time axis 511. The acoustic reflections at the anterior cornea surface 512, Bowman's interface 513 and the posterior cornea surface 514 are shown. Typically the reflection at the anterior cornea surface 512 is a higher amplitude than the reflection at the posterior cornea surface 514 because of signal attenuation, and the amplitude of the reflection at Bowman's interface 513 is relatively low because of the small change in acoustic impedance at Bowman's interface as compared to the change in acoustic impedance at the anterior cornea surface 512 or the posterior cornea surface 514.

It is noted that in practice, there are often large acoustic reflections from the hygienic barrier or membrane (item 206 in FIG. 2) which separates the water chamber in which the transducer and arc guide assembly are contained from the water in which the patients eye is immersed. The reflections from this membrane are irregular depending on wrinkles in the membrane material. The timing of these reflections is known and they are removed from the A-scan data by software algorithms.

A B-scan is a processed derivative of an A-scan constructed by either or both of converting it from a time to a distance using acoustic velocities or by using grayscales which correspond to A-scan amplitudes to highlight the features along the A-scan time history trace. Typically, the higher the amplitude, the brighter the point assigned to the B-scan. Zero amplitude is typically black and brightness increases to a maximum in increments typically ranging from 128 to 1,024. Thus interfaces such as the anterior cornea surface 512 and the posterior cornea surface 514 show up as bright spots along the beam path and Bowman's interface 513 as a less bright spot along the beam path. When all the B-scans are corrected for the angle of the transducer along the arc; the time co-ordinates changed to spatial co-ordinates using local acoustic velocities; and results plotted in the correct spatial relation to each other, they will form a geometrically correct image of the corneal layers. Software algorithms are typically used to interpolate between adjacent B-scans to produce a continuous image. In order for a set of B-scans to be able to produce an image with components that are sharply delineated and of reasonably equal brightness, the individual A-scans should be taken at substantially equal distances from the surface of the eye component of interest and at a substantially normal angle to the surface of the eye component of interest. These requirements can be optimized by known alignment procedures which are described in some detail in FIGS. 5 through 9. B-scans and images derived from them are illustrated and discussed in more detail in "Ultrasonography of the Eye and Orbit".

Ultrasonic Scanning Procedures

Figure 6A:
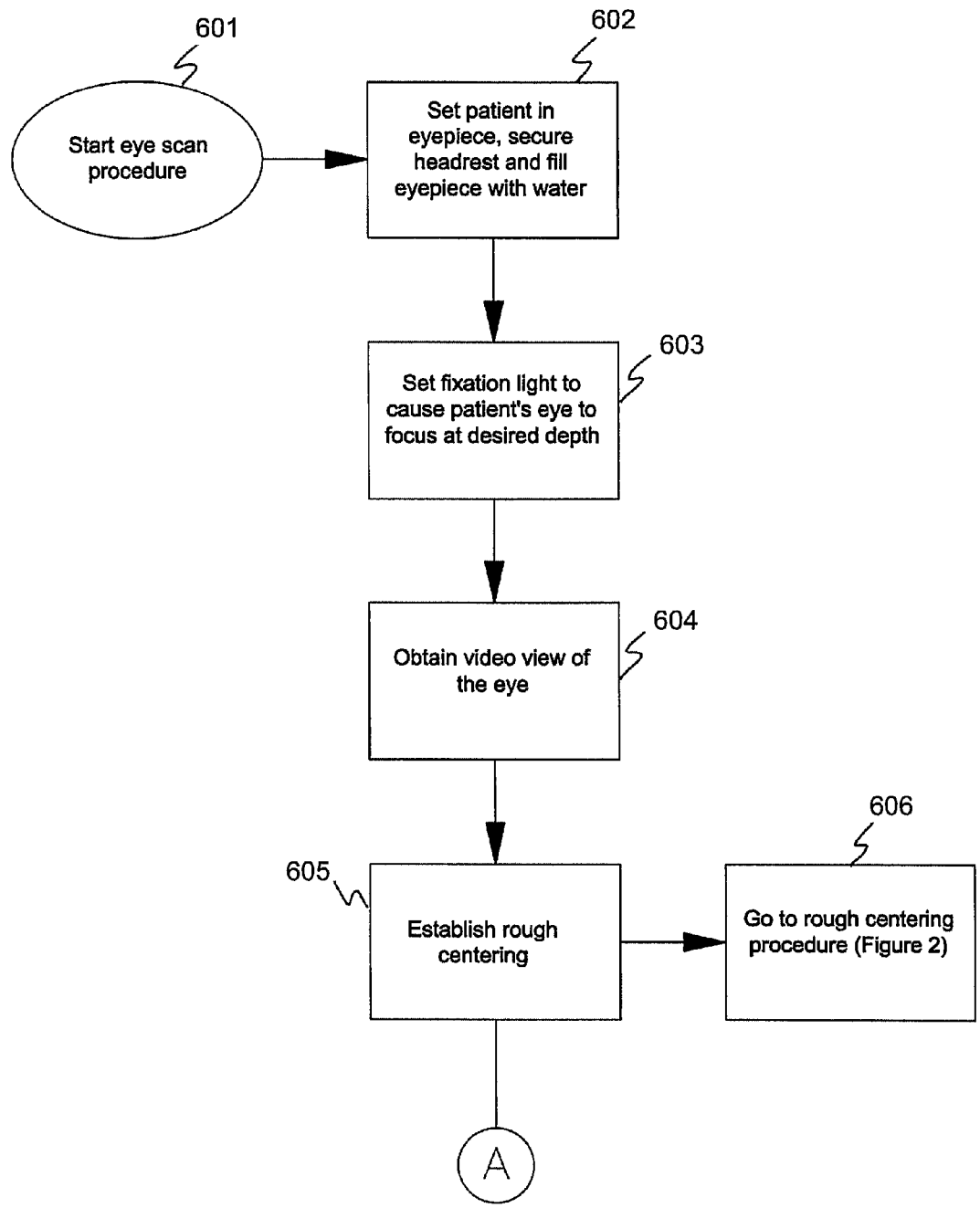
FIG. 6a and FIG. 6b are flow charts of a sequence of operations for obtaining an accurate B-scan set.
Figure 6B:
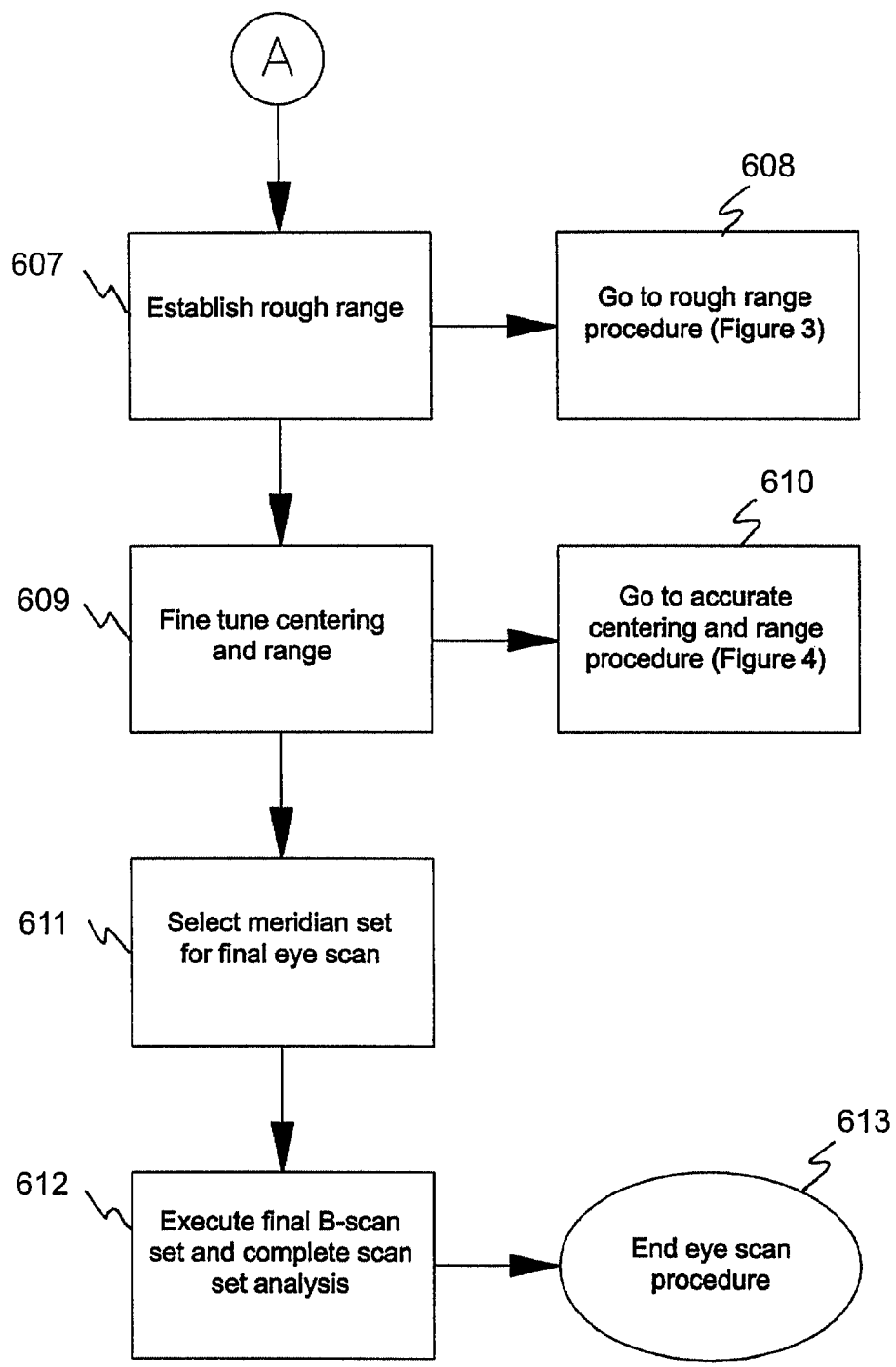

FIG. 6a and FIG. 6b are flow charts of a sequence of operations for obtaining an accurate B-scan set. This is one of a number of possible sequences of operations to obtain an ultrasonic image of an eye and is the sequence of procedures currently used by arc scanning devices. In FIG. 6a, the scan procedure begins at step 601. The patient is seated in front of the scanner during step 602, places their head in a headrest with their eye pressed into a disposable eyepiece. When the headrest is secured, the eyepiece is filled with warm water so as to provide a continuous acoustic path in water from the transducer to the surface of the patient's eye. Typical eyepieces are disclosed in U.S. patent application Ser. No. 12/347,674. Conventional and advanced headrest apparatuses are described in US Provisional Application Serial Number 61/109,069 filed on Oct. 28, 2008, entitled "Method of Positioning a Patient for Medical Procedures" which is incorporated herein by reference. Next, in step 603, a fixation light is positioned so that the patient's eye focuses at a desired distance along the patient's optical axis. The fixation light is typically a small bright dot of light that is easily seen by the patient and the position of this fixation light is preferably adjustable along the patient's optical axis so as to cause the patient's eye to focus at a desired distance. This distance can be at infinity such as might be used for a corneal or lens scan or it might be as close as about 1 meter such as might be used for a scan of an accommodating lens. In step 604, a video image of the patient's eye is formed on the scanner's computer video monitor screen. This video image will typically show the eyepiece filling with water and the patient's eye blinking as the patient's eye adjusts to the water. Once the patient adjusts to the water, their eye can remain open. In step 605, a rough centering of the transducer and arc track are obtained step 606 which is more fully described in the flow chart of FIG. 7.

Steps 601 through 606 are typically controlled by the operator who interacts with the arc scanning machine using a mouse and/or keyboard and computer video screen to input information into the scanner's computer. This process is more fully described in FIG. 10.

Figure 10:
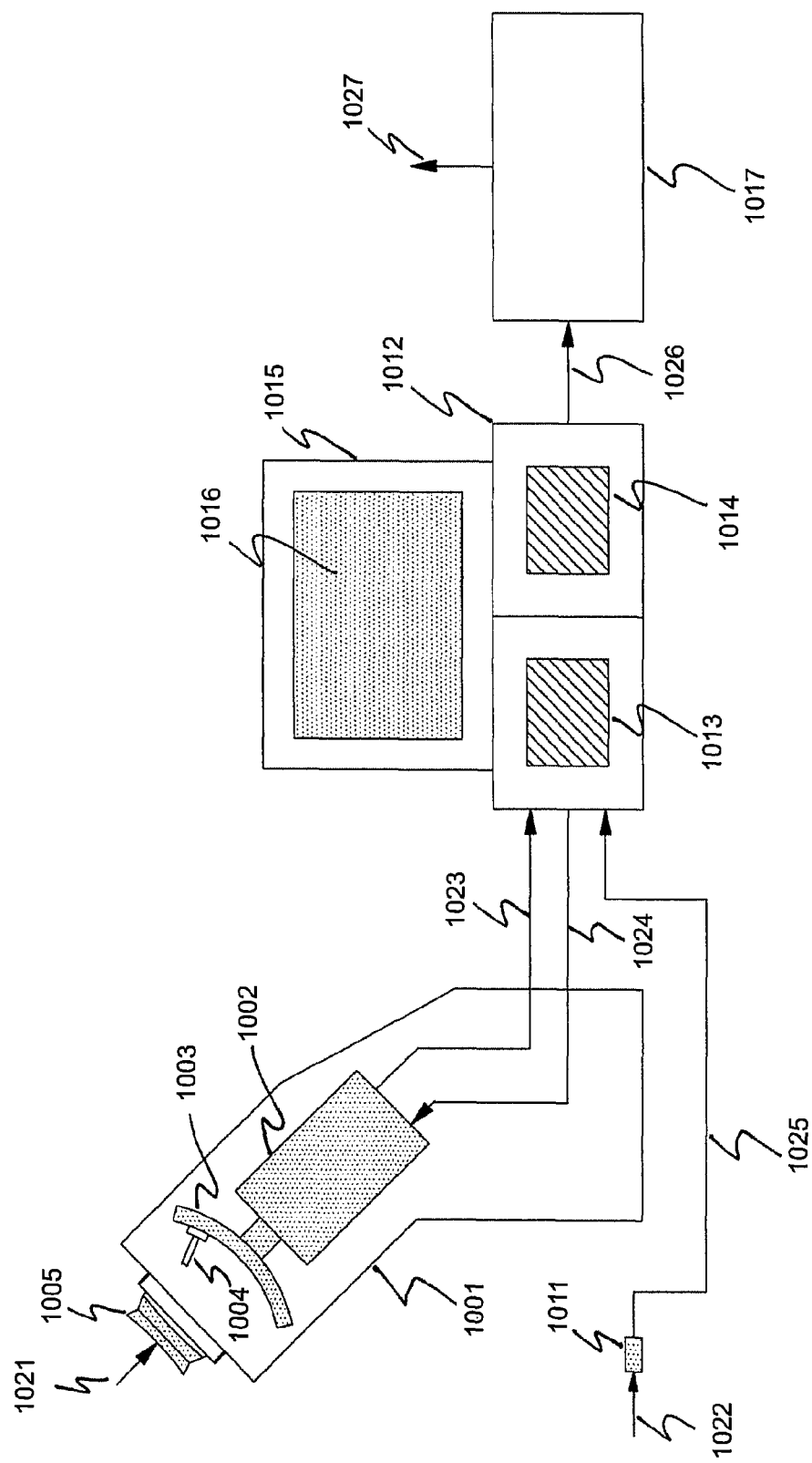
FIG. 10 is a schematic representation of the control functions of an arc scanning apparatus.

Steps 607 through 613 may be controlled by the operator or they may be completed under computer processor control as discussed in FIG. 10.

The flow chart of FIG. 6a continues in FIG. 6b as indicated. In step 607, the rough range of the transducer aperture with respect to the eye component of interest is established step 608 which is more fully described in the flow chart of FIG. 8. In step 609, the arc track is accurately centered with respect to the eye surface of interest and the range or focal plane of the transducer aperture is accurately adjusted, if necessary, with respect to the eye component of interest. Accurate centering and range procedures, step 610, are more fully described in the flow chart of FIG. 9a and FIG. 9b. A prime scan meridian is selected in step 606 (the rough centering procedure). In step 611, a set of scan meridians are selected by the operator, if they have not already been pre-selected in the scan set-up procedure before the patient has been seated. These are typically a set of meridians where the arc track is rotated about its center of curvature through a set of desired angles from the prime meridian. For example, if the prime meridian is at 0 degrees (typically horizontal), a set of meridians might consist of the prime meridian, meridians rotated clockwise 15 and 30 degrees from the prime meridian and meridians rotated counterclockwise 15 and 30 degrees from the prime meridian (a five meridian scan set). Once this meridian set has been selected in step 611, the scanner automatically executes a series of B-scans along each meridian of the selected meridian set in step 612 and continues automatically with the various types of analyses available. These analyses might include full images along each meridian and, using all the data from all the meridian scans, preparation of thickness maps of the eye component of interest. The scanning session is completed in step 613 and the water is drained from the eyepiece. This sequence completes the acoustic scan of the patient's eye.

In prior art arc scanners, this sequence of operations requires that the operator manually move the scan head assembly for the centering and focusing steps. The scan head positioning device described in FIG. 3 can accomplish these operations under computer control which can be programmed to rapidly go through any number of selected sequence of movements. This allows the centering and focusing operations to be executed swiftly in typically about 1 or 2 seconds. The computer controlled sequence can then continue to make images for several meridians typically in sets of 1, 3, 5 etcetera to a scan set of 11 meridians or more. The entire procedure from step 605 to step 612 can be completed in several seconds and thereby minimize the chance that the patient moves their eye, changes focus of their eye or blinks. If the resultant images are unacceptable to the operator, then they may be easily repeated. The time in which this sequence of operations may be performed is limited by the requirement that the motions of the scan head assembly not be so rapid as to cause significant disturbance of the water in which the scan head assembly is immersed since this can lead to bubbles forming on, for example, the transducer face or eyepiece membrane which, in turn, can decrease the quality of the images obtained. This requirement is usually not violated with rapid movements of the scan head positioner or transducer movement along the arc track as currently practiced where an entire sequence of focusing, centering and scanning motions are executed in from about 1 to about 5 seconds.

Figure 7:
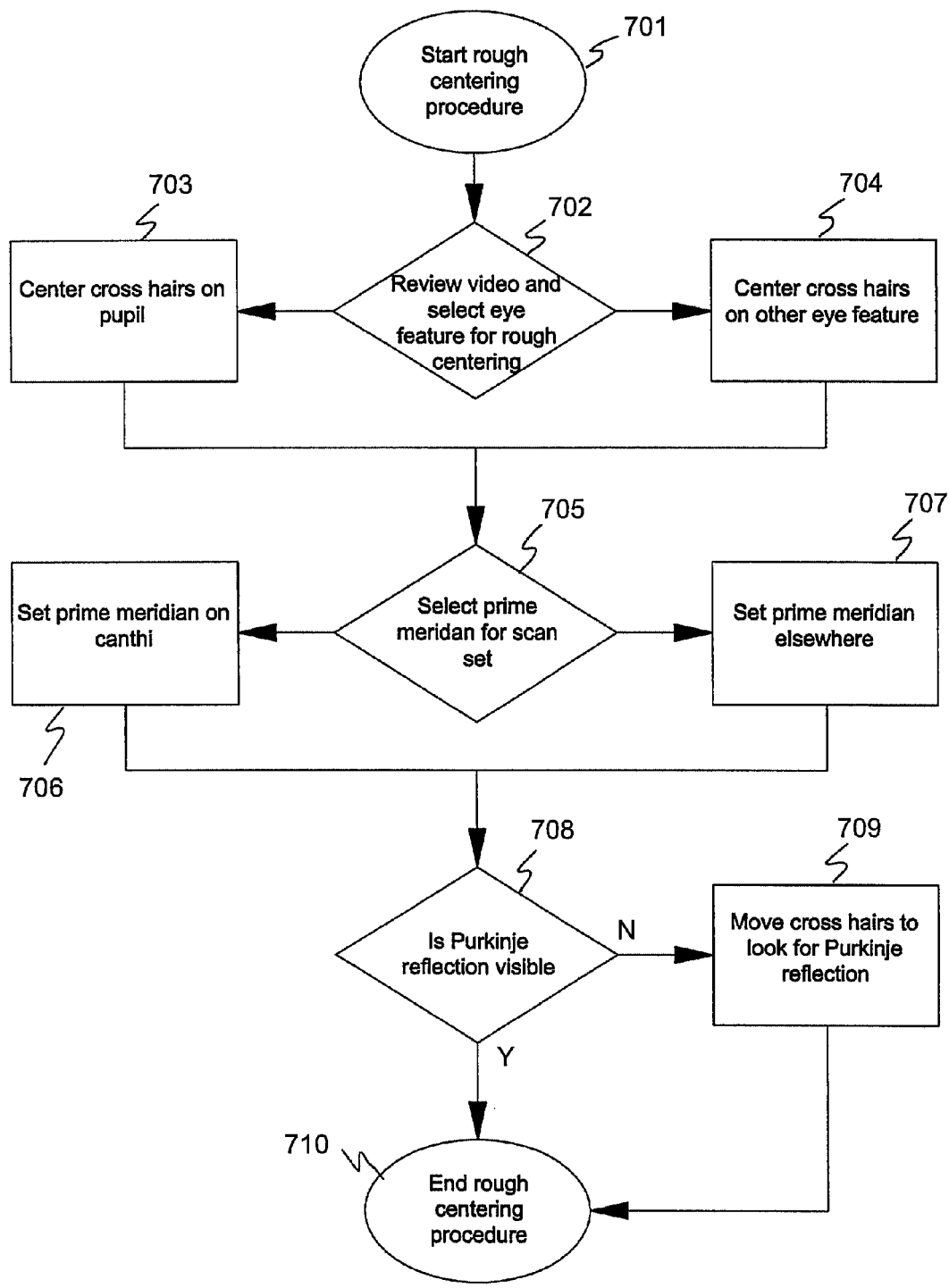
FIG. 7 is a flow chart of a sequence of operations for rough centering.

FIG. 7 is a flow chart of a sequence of operations for rough centering which begins with step 701. In step 702, the video image of the patient's eye is reviewed on the scanner's computer video monitor and the operator selects an eye feature to use for rough centering, The operator may select centering a set of cross hairs which appear on the video image at the center of the pupil as in step 703 or the operator may select another eye feature such as a blood vessel, scar etcetera on which to center the cross hairs as in step 704. Next the operator selects the orientation of the prime meridian of the arc track in step 705. This may be a meridian that is horizontal and goes from the nasal side canthus to the temporal side canthus as in step 706. Alternately, in step 707, the prime meridian may be oriented at any desired angle from 0 to 90 degrees from the substantially horizontal canthus to canthus line. For example, such an alternate selection may be required to best scan a diseased feature of the eye. In step 708, if the first (strongest) Purkinje reflection is seen in the video view of the eye, then the rough centering procedure is completed step 710. If the first Purkinje reflection is not seen in the video view of the eye, the cross hairs may be moved around (typically with a mouse or touch screen control but also by an automated search algorithm) by the operator in step 709 until a first Purkinje reflection is observed and then the rough centering procedure is completed step 710. In some cases, the first Purkinje reflection may not be seen and the operator may choose to proceed to step 710 ending the rough centering procedure. In this process, the transducer carriage has been moved along the arc track, away from its central position and parked so that the patient can clearly see the fixation light target when the fixation target is located along the z-axis of the scan head positioning apparatus.

Figure 8:
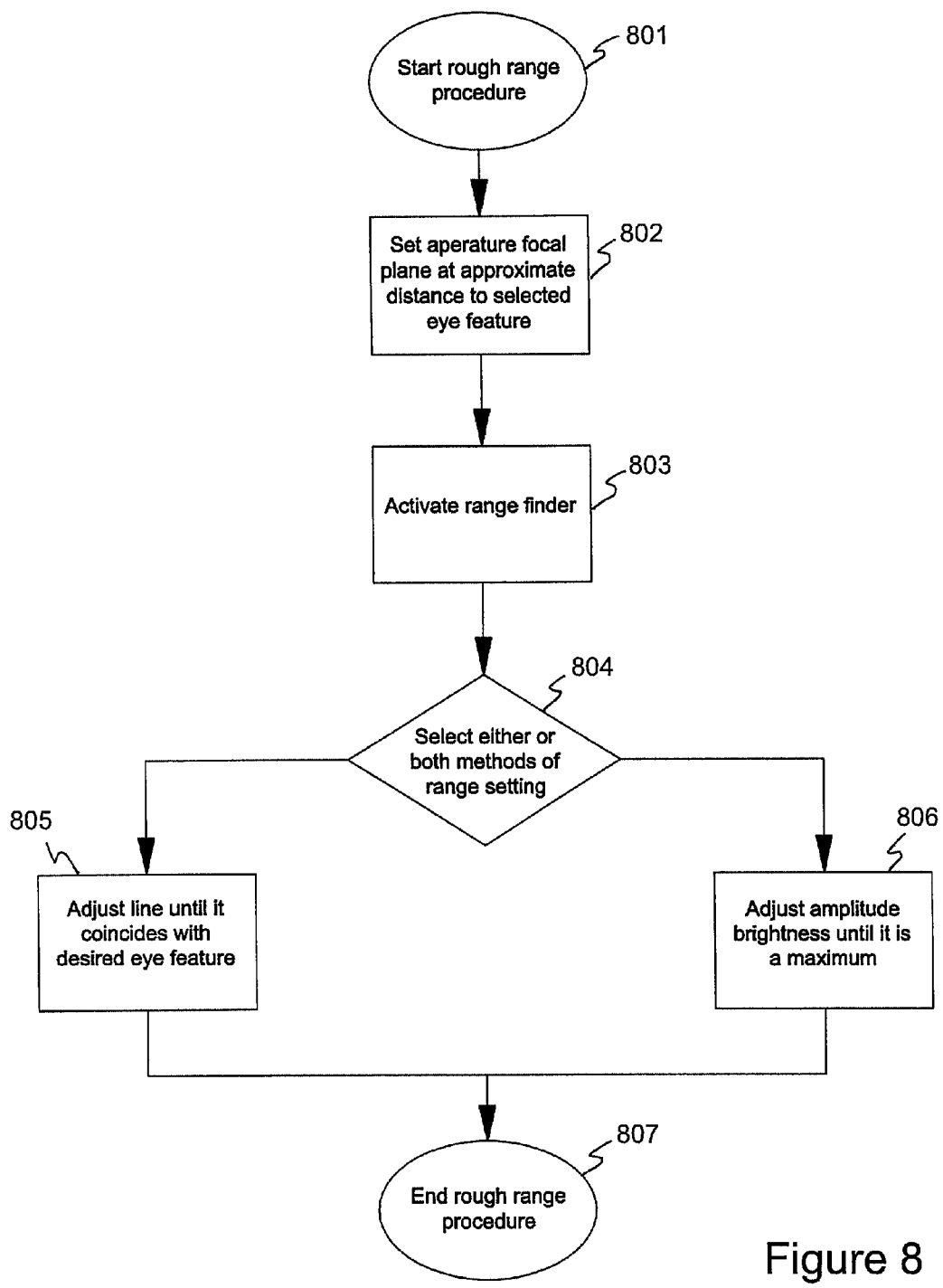
FIG. 8 is a flow chart of a sequence of operations for rough range finding.

FIG. 8 is a flow chart of a sequence of operations for rough range finding beginning with step 801. In step 802, the operator sets the transducer aperture at the approximate location with respect to the eye component of interest. This can be done by dead reckoning when the operator is familiar with the parked position of the arc track and the focal length of the transducer. In step 803, the operator selects a range finder sub-screen on the scanner's monitor. This activates a continuous A-scan of the eye which is shown on the sub-screen along with a line that represents the focal plane of the transducer aperture. The location of this line is set in the scanning software by entering the focal length of the transducer aperture. The operator can usually determine the A-scan representation of eye feature on which to place the aperture focal plane (for example Bowman's layer may be selected for a corneal scan and Bowman's layer appears as a small peak directly after the anterior surface of the cornea (see FIG. 5 for example). In step 804, the operator selects one of two methods of setting the focal plane of the aperture on the desired eye feature. If step 805 is selected, the operator may move the arc track in and out (the z-direction shown in FIG. 3) using a mouse, keyboard or touch screen control causing the line that represents the focal plane of the transducer aperture to move onto the desired eye feature or the operator may move the arc track in and out using mouse, key board or touch screen control causing the A-scan representation of the desired eye feature to brighten or dim as in step 806. By selecting the position where the A-scan representation of the desired eye feature is brightest, the operator knows that the focal plane is located where it is desired. The operator may use either or both methods of rough focusing. Usually both methods will indicate the same focal depth location at the same time. If both methods do not indicate focus at the same location, the method of step 806 is preferable since it is inherently accurate and tells the operator that the focal plane is located where desired. The line that represents the focal plane of the transducer aperture may be in error, for example, if the focal length of the transducer was improperly entered into the scanner's control software. Once step 805 and/or 806 is completed, the process proceeds to step 710 ending the rough range finding procedure.

Figure 9A:
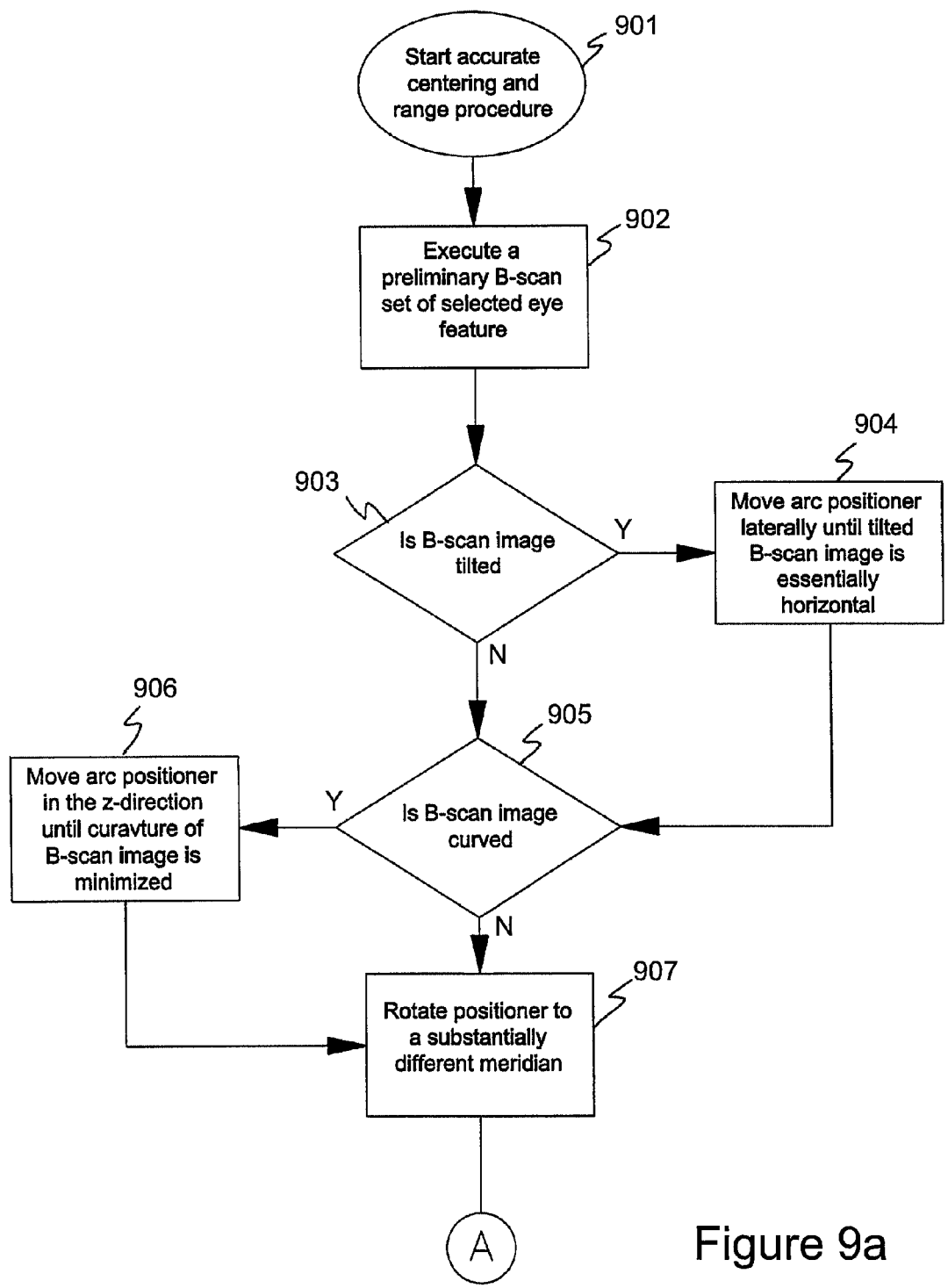
FIG. 9a and FIG. 9b are flow charts of a sequence of operations for accurate centering and range finding.
Figure 9B:
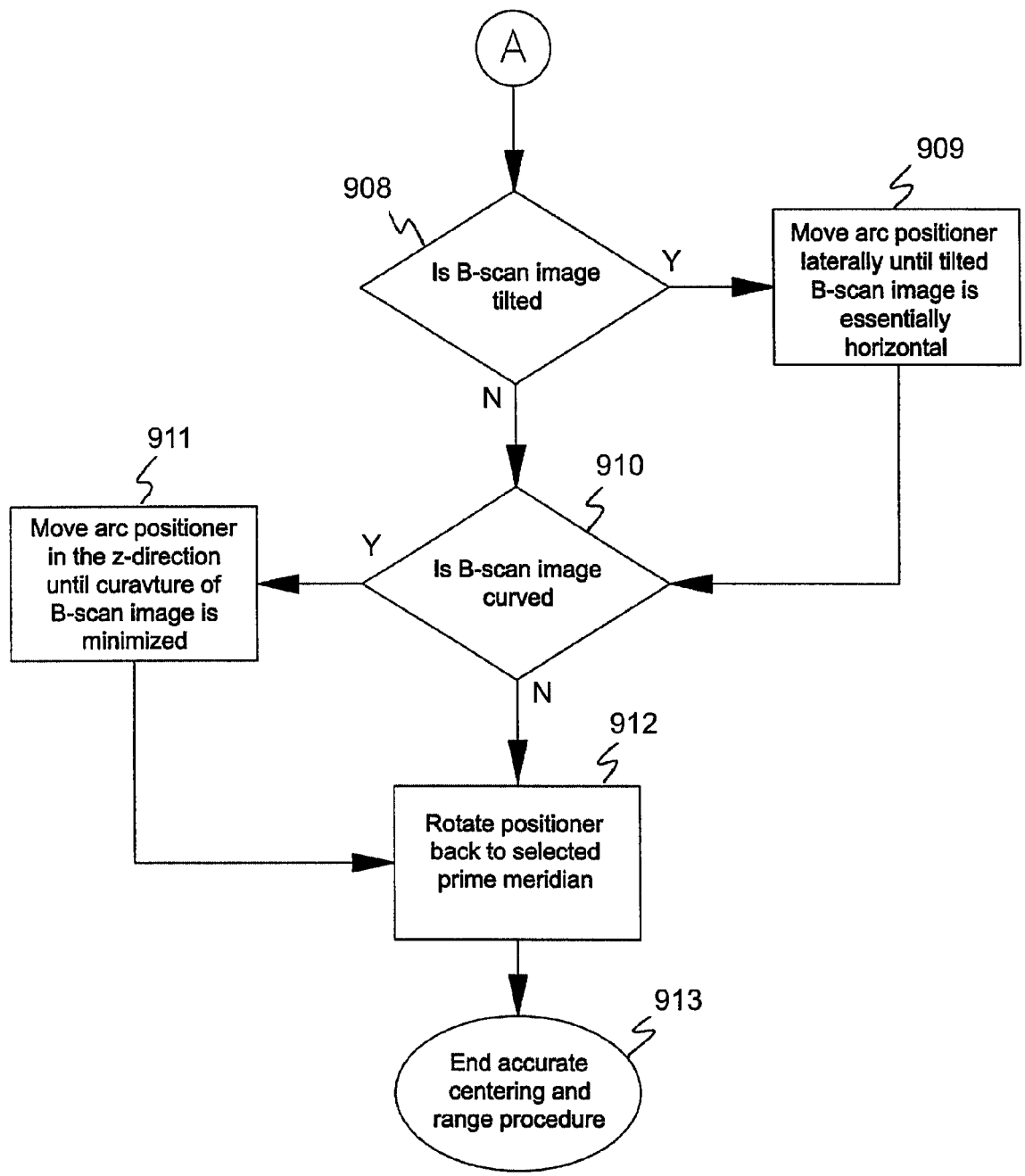

FIG. 9a and FIG. 9b are flow charts of a sequence of operations for accurate centering and range finding. In FIG. 9a, the sequence begins with step 901. In step 902, the operator executes a set of preliminary B-scans, typically along the prime meridian. These are typically geometrically uncorrected B-scans and are refreshed continuously. These may cover an arc with included angle up to about half of the total included angle along the arc track and are typically centered about the center of the arc track. If the cornea is being imaged, then the B-scan set will form an image of the cornea including the anterior and posterior surfaces, usually Bowman's layer and possibly other layers within the cornea such as for example a LASIK flap. In step 903, if the B-scans are horizontal then the arc track is centered laterally and the operator proceeds to step 905. If the B-scans are tilted from the horizontal, then the transducer is not centered laterally with respect to the center of curvature of the eye component. If this is the case, then the operator proceeds to step 904 and moves the arc track laterally back and forth until the B-scans are substantially horizontal. When the B-scans are substantially horizontal, the acoustic pulses are passing very closely through both the center of curvature of the eye component of interest and the center of curvature of the arc track. In step 905, if the B-scans are not substantially curved then the arc track is focused vertically and the operator proceeds to step 907. If the B-scans are curved, then the transducer is not focused vertically with respect to the center of curvature of the eye component. If this is the case, then the operator proceeds to step 906 and moves the arc track vertically in and out until the B-scans are substantially uncurved (some curvature is acceptable since the curvature of the arc track is not exactly the same as the curvature of the eye surface of interest). When the B-scans are substantially uncurved or the curvature is minimized, the center of curvature of the eye component of interest and the center of curvature of the arc track are essentially coincident since the lateral offset has already been corrected, if necessary, in step 904. The arc track has now been centered and focused accurately with respect to the prime meridian. In step 907, the arc track is rotated through a substantial angle with respect to the prime meridian, typically 90 degrees with respect to the prime meridian but the angle may be less depending on the operator's objective.

The flow chart of FIG. 9a continues in FIG. 9b as indicated. Steps 908 through 911 are essentially repeats of steps 903 through 906 except that they are carried out along a new meridian. This then ensures that the arc track is centered and focused accurately with respect to the eye component of interest in at least 2 meridians at substantially different angles. In step 912, the arc track is returned to the prime meridian and the accurate centering and range procedure is ended in step 913.

In the preceding discussion of procedures in FIGS. 6 through 9, reference was made to a number of operator selections and actions. As can be appreciated, these selections and actions can be automated. Specifically, operations 607 through 613 of FIG. 6b, which include all the selections and operations of FIGS. 8 and 9, can be automated under computer control. This is possible because all the motions possible with the scan head positioning assembly (See FIG. 3) are automated and can be prescribed by a computer program. Conventional ultrasonic scanning techniques and algorithms are currently limited in that most require expert users to manually move some of the elements of the scan head positioning apparatus for alignment which requires the patient to remain longer with their eye immersed in water. This can result in substandard images due to patient movement, especially of the eye. In the present invention, all of these critical centering and focusing procedures can be automated because the motions of scan head positioning assembly can be prescribed by a computer program. This capability enables rapid and often complex imaging sequences to be completed before the patient becomes uncomfortable, thus minimizing the likelihood of patient eye movement during the scanning procedure which, in turn, results in blurring of portions of the image and introducing inaccuracies into the images.

FIG. 10 is a schematic representation of the control functions of an arc scanning apparatus. The arc scanning apparatus is comprised of an arc scanning machine 1001 which includes an arc guide positioning mechanism 1002, an arc guide (or arcuate guide or arc track) 1003, an ultrasonic transducer 1004 and a disposable eyepiece 1005. The arc scanning machine 1001 is connected to a computer 1012 which includes a processor module 1013 and a memory module 1014 and a video monitor 1015 with video screen 1016. The computer 1012 is connected to an operator input device such as a mouse 1011 and/or a keyboard (not shown). The computer 1012 is also connected to an output device such as, for example, a printer or internet connection 1017. The patient is seated at the machine 1001 with their eye engaged with disposable eyepiece 1005 such as described in FIG. 2. The patient's eye component to be imaged is represented by input 1021. The operator using mouse and/or keyboard 1011 and video screen 1016 inputs information 1022 into computer 1012 selecting the type of scan and scan configurations as well as the desired type of output analyses. The operator, using mouse and/or keyboard 1011, a video camera (see item 223 in FIG. 2) in scanning machine 1001 and video screen 1016, then centers a set of cross hairs displayed on video screen 1016 on the desired component of the patient's eye, also displayed on video screen 1016, setting one of the cross hairs as the prime meridian for scanning. Once this is accomplished, the operator instructs computer 1012 using either mouse and/or keyboard 1011 to proceed with the scanning sequence. Now the computer processor 1013 takes over the procedure and issues instructions via path 1024 to the positioning head 1002, the arc track 1003 and the transducer carriage 1005 and receives positional and imaging data via path 1023 which is stored in memory module 1014. The computer processor 1013 proceeds with a sequence of operations such as for example: (1) rough focus transducer 1004 on the selected eye component; (2) accurately center arc track 1004 with respect to the selected eye component; (3) accurately focus transducer 1004 on the selected feature of the selected eye component; (4) rotate the arc track through a substantial angle and repeat steps (1) through (3) on a second meridian; (5) rotate the arc track back to the prime meridian; (6) initiate a set of A-scans along each of the of selected scan meridians, storing this information in memory module 1014; (7) utilizing processor 1013, converting the A-scans for each meridian into a set of B-scans and then processing the B-scans to form an image associated with each meridian; (8) performing the selected analyses on the A-scans, B-scans and images associated with each or all of the meridians scanned; and (9) outputting 1027 the data in a preselected format to an output device such as printer 1017. The output can also be stored in memory module 1014 for later retrieval on video screen 1016, or for transmission to remote computers or other output devices via any number of well-known data transmission means.

A-Scan Gain Control

In accordance with at least some embodiments of the present invention, the method of determining the distance from a transducer aperture to a particular surface of the eye or relative distances between surfaces begins when the aperture takes a first A-scan along a first vector. A "vector" refers to a single A-scan amplitude-time history obtained from a transducer aperture when the aperture is in a known, fixed position on the arc along which it traverses. The emitted ultrasonic wave reflects off of the various surfaces in the eye and amplitude data of the reflected ultrasonic wave is captured such that a first A-scan waveform is generated. After the first waveform is generated, the method continues with the aperture being slightly repositioned along the arc track. In accordance with one embodiment of the present invention, the aperture may be moved an insignificant distance such that an A-scan waveform captured from the second position is essentially the same as an image captured from the first position. More specifically, the aperture may traverse an arc for a total angular travel of about 70 degrees of motion as it scans along a single meridian. Typically, about 128 to about 1,024 vectors per scan meridian can be captured to obtain a relatively complete set of vectors for that range of motion across the meridian. Each vector is about 60 microns wide and the average cornea has a radius of about 1,200 microns. In accordance with at least some embodiments of the present invention, if, for example, 512 vectors per meridian are captured, then subsequent adjacent vectors will have a substantial amount of overlap to the point that each vector effectively captures an image from the same location as the previous vector. Thus, during the reposition step, the aperture may be moved about $1/512$ of the distance that it will traverse along the arc.

Once the aperture has been "repositioned", the method continues by adjusting the gain associated with the second scan. This gain may be controlled at the user interface via the independent gain controls where each control effects the gain of every-other vector. Thus, the gain specified in the first gain control may be used during scans at the first, third, fifth, seventh, and any other odd scan while the gain specified in the second gain control may be used during the second, fourth, sixth, eighth, and other even scans. After the gain has been adjusted, a second scan is taken at the second position. The second scan may result in a second A-scan waveform being generated that is effectively the same scan as the first scan, but with a different gain. The different gain allows features having different reflective properties to be more easily seen. More specifically, if the second scan was taken using a higher gain than the first scan, then the second scan will show the portions of the first scan that were lost in the noise. For example, the first waveform may clearly display the peaks representing the position of surfaces that are highly reflective. However, the surfaces that are not highly reflective, such as for example an old LASIK flap scar, may not be easily discernable from the first waveform. The second waveform, however, depicts the peaks and locations of the lesser reflective surfaces but the peaks corresponding to the highly reflective surfaces are lost beyond the gain threshold. The two waveforms may be combined into a composite waveform that effectively depicts the peaks of both the first and second waveforms. Thus the highly reflective peaks can be seen on the same composite waveform as the lesser reflective peaks and distances between the peaks can be measured to more accurately determine the distance between surfaces of the eye. This may provide an increased accuracy in distance measurements between the various surfaces of the eye.

Besides the use of differential gains for alternating vectors, the scanning device may alternately or further be equipped with a 2-channel digitizer in accordance with at least some embodiments of the present invention. More specifically, since multiple gains are desired for various vectors captured by the aperture, a digitizer is used to generate the images. In one embodiment, the digitizer may include a pre-amplifier for conditioning the voltage signal generated at the aperture as a result of receiving reflected ultrasonic waves. After passing the received signal through the pre-amplifier, the signal may be split. The first signal may be passed through a first gain amplifier that amplifies the signal by a first amount whereas the second signal may be passed through a second gain amplifier that amplifies the signal by a second different amount. The resulting signals will have different characteristics and likely produce two seemingly different waveforms. The signals may then be passed through a Digital-to-Analog converter ("DACs") respectively and may be provided as output for a user interface that depicts the waveforms captured by the aperture. The DACs may be operated by a common clock to maintain consistency of the analog signals, thereby making the composite signal more accurate.

Improvement of Measurement Accuracy

In accordance with at least another embodiment of the present invention, a method of determining the distance from an aperture to a particular surface of the eye or relative distances between surfaces of the eye is provided. The method improves on previous distance determining methods that introduced distance errors on the order of tens of microns. Such errors are introduced because prior art distance determining methods relied upon the use of pixels in the image to determine surface distance. Thus, the size of the pixels limited the extent to which distance could be accurately computed. In accordance with embodiments of the present invention, an A-scan and/or a de-convolution of the A-scan is used to determine distances between surfaces of the eye. In a de-convoluted A-scan, the signals characteristic of a particular transducer are removed from the original A-scan. These signal characteristics are determined from a separate experiment from which these characteristic are measured and stored. More specifically, amplitude data that is obtained from such A-scans can be analyzed to determine the location, and thus, relative distances between various surfaces of the eye. Since amplitude data of an ultrasonic wave is used rather than image pixels, the errors introduced to distance calculations is greatly reduced. In accordance with at least one embodiment of the present invention, independent brightness control/power/gains can be used on sequential vectors of a scan to more accurately determine the distance between surfaces.

A number of variations and modifications of the inventions can be used. As will be appreciated, it would be possible to provide for some features of the inventions without providing others. For example, though the embodiments are discussed with reference to an arc scanning device, it is to be understood that the various embodiments may be used with other types of scanning devices, such as sector scanning devices or other ultrasonic scanners using different transducer motion strategies.

The present invention, in various embodiments, includes components, methods, processes, systems and/or apparatus substantially as depicted and described herein, including various embodiments, sub-combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, for example for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An ocular imaging method, comprising:
    (a) receiving, from an operator, a selection of at least one feature of a patient's eye, a set of scan meridians comprising a prime scan meridian and one or more secondary scan meridians, and a set of scan analysis instructions;
    (b) receiving, from an operator, a selection of a center location of an ultrasonic transducer relative to the at least one selected feature of the patient's eye;
    (c) determining, by a processor, a first range of an ultrasonic transducer aperture relative to the at least one selected feature of the patient's eye;
    (d) moving, by a processor, a position of at least one of an ultrasonic transducer and arcuate guide relative to the at least one selected feature of the patient's eye;
    (e) determining, by a processor, a predetermined range of the at least one of an ultrasonic transducer and arcuate guide relative to the at least one selected feature of the patient's eye;
    (f) executing, based on the set of scan meridians, a series of ultrasonic scans of the patient's eye; and
    (g) executing, based on the set of scan analysis instructions, at least one of a set of acoustic images for each selected scan meridian, a set of eye component thickness maps, and major dimensions of the selected eye components.

2. The method of claim 1, wherein step (c) comprises the sub-steps:
    (C1) performing a series of ultrasonic A-scans;
    (C2) determining an A-scan representation of the selected feature of the patient's eye; and (C3) setting a focal plane of the ultrasonic transducer aperture on the A-scan representation.

3. The method of claim 1, wherein step (d) comprises the sub-steps:
    (D1) executing a series of B-scans along the prime meridian;
    (D2) determining from a selected B-scan whether or not the arcuate guide is centered laterally and automatically move the arcuate guide by applying the following rules:
        (i) when the selected B-scan is horizontal, the arcuate guide is centered laterally; and
        (ii) when the selected B-scan is not horizontal, the arcuate guide is not centered and the processor causes automated lateral movement of the arcuate guide until the selected B-scan is horizontal;
    (D3) determining from a selected B-scan whether or not the arcuate guide is centered vertically and automatically move the arcuate guide by applying the following rules:
        (i) when the selected B-scan is not curved, the arcuate guide is centered vertically;
        (ii) when the selected B-scan is curved, the arcuate guide is not centered vertically and the processor causes automated vertical movement of the arcuate guide until the selected B-scan is uncurved; and
    (D4) rotating the arcuate guide through an angle from the prime meridian to a second meridian; and
    (D5) repeating steps (D1)-(D3) with respect to the second meridian and then returning the arcuate guide to the prime meridian.

4. The method of claim 1, wherein, in step (a), a type of scan to be performed is received from an operator and further comprising:
    (h) selecting a scan configuration from a plurality of scan configurations associated with differing types of scans, the various scan configurations comprising differing configuration parameters.

5. The method of claim 1, further comprising:
    (h) determining a distance from the ultrasonic transducer aperture to a selected surface of the patient's eye by performing the following substeps:
    (H1) at a first aperture position and using a first gain, taking a first scan along a first vector;
    (H2) receiving a reflected ultrasonic wave; and
    (H3) forming a first waveform from the reflected ultrasonic wave;
    (H4) repositioning the aperture to a second aperture position and repeating steps (H1)-(H3) with respect to the second aperture position and using a second gain; and
    (H5) combining the waveforms to form a composite waveform.

6. The method of claim 1, wherein step (g) comprises:
    (G1) receiving reflected waves from a scan;
    (G2) splitting the reflected waves into first and second waves;
    (G3) applying a first gain to the first wave; and
    (G4) applying a second gain to the second wave.

7. The method of claim 1, further comprising:
    (h) generating, from the ultrasonic scans, distances between the selected features of the patient's eye, the distances being determined by the time interval between the peak-to-peak amplitudes of the selected features converted to distances by multiplying the time intervals by a local acoustic velocity between the selected features.

8. The method of claim 1, wherein the selected feature is at least one of a cornea, a natural lens, an artificial lens, an iris, a retina, diseased ocular tissue, damaged ocular tissue and injured ocular tissue, and further comprising:

moving a fixation light to change a degree of focus of the patient's eye.

9. An ocular imaging system, comprising:
   an ultrasound transducer;
   an arcuate guide for the ultrasound transducer;
   a plurality of positional displacement devices to displace the arcuate guide and the transducer to a selected position and orientation;
   an operator input, the operator input comprising at least one of a selection of at least one feature of a patient's eye, a set of scan meridians comprising a prime scan meridian and a plurality of secondary scan meridians, and a set of scan analysis instructions; and
   a processor operable to perform the following operations:
   (a) determine a first range of an ultrasonic transducer aperture relative to the selected feature of the patient's eye;
   (b) center and move the ultrasonic transducer and arcuate guide relative to the selected feature of the patient's eye;
   (c) determine a predetermined range of the ultrasonic transducer aperture relative to the selected feature of the patient's eye;
   (d) execute, based on the set of scan meridians, a series of ultrasonic scans of the patient's eye; and
   (e) execute, based on the set of scan analysis instructions, at least one of a set of acoustic images for each selected scan meridian, a set of eye component thickness maps, and major dimensions of the selected eye components.

10. The system of claim 9, wherein operation (b) comprises the sub-operations:
   (B1) perform a series of ultrasonic A-scans;
   (B2) determine an A-scan representation of the selected feature of the patient's eye; and
   (B3) set a focal plane of the ultrasonic transducer aperture on the A-scan representation.

11. The system of claim 9, wherein operation (c) comprises the sub-operations:
   (C1) execute a series of B-scans along the prime meridian;
   (C2) determine from a selected B-scan whether or not the arcuate guide is centered laterally and automatically move the arcuate guide by applying the following rules:
      (i) when the selected B-scan is horizontal, the arcuate guide is centered laterally; and
      (ii) when the selected B-scan is not horizontal, the arcuate guide is not centered and the processor causes automated lateral movement of the arcuate guide until the selected B-scan is horizontal;
   (C3) determine from a selected B-scan whether or not the arcuate guide is centered vertically and automatically move the arcuate guide by applying the following rules:
      (i) when selected B-scan is not curved, the arcuate guide is centered vertically;
      (ii) when the selected B-scan is curved, the arcuate guide is not centered vertically and the processor causes automated vertical movement of the arcuate guide until the selected B-scan is uncurved; and
   (C4) rotate the arcuate guide through an angle from the prime meridian to a second meridian; and
   (C5) repeating operations (C1)-(C3) with respect to the second meridian and then returning the arcuate guide to the prime meridian.

12. The system of claim 9, wherein a type of scan to be performed is received from an operator and wherein the processor further:
   (f) selects a scan configuration from a plurality of scan configurations associated with differing types of scans, the various scan configurations comprising differing configuration parameters.

13. The system of claim 9, wherein the processor further:
   (f) determines a distance from the ultrasonic transducer aperture to a selected surface of the patient's eye by performing the following sub-operations:
   (F1) at a first aperture position and using a first gain, take a first scan along a first vector;
   (F2) receive a reflected ultrasonic wave; and
   (F3) form a first waveform from the reflected ultrasonic wave;
   (F4) reposition the aperture to a second aperture position and repeat steps (G1)-(G3) with respect to the second aperture position and using a second gain; and
   (F5) combine the waveforms to form a composite waveform.

14. The system of claim 9, further comprising:
   a splitter adapted to receive, at an input, reflected waves from a scan and split the reflected waves into first and second waves; and
   first and second gain amplifiers adapted to apply, respectively, a first gain to the first wave and a second gain to the second wave.

15. The system of claim 9, wherein the processor generates, from the ultrasonic scans, distances between the selected features of the patient's eye, the distances being determined by the time interval between the peak-to-peak amplitudes of the selected features converted to distances by multiplying the time intervals by a local acoustic velocity between the selected features.

16. The system of claim 9, wherein the selected feature is at least one of a cornea, a natural lens, an artificial lens, an iris, a retina, diseased ocular tissue, damaged ocular tissue and injured ocular tissue, and further comprising:
   a movable fixation light to change a degree of focus of the patient's eye.

17. An ocular imaging method, comprising:
   (a) receiving, from an operator, a selection of at least one feature of a patient's eye, a set of scan meridians comprising a prime scan meridian and one or more secondary scan meridians, and a set of scan analysis instructions;
   (b) receiving, from an operator, a selection of a center location of an ultrasonic transducer relative to at least one selected feature of the patient's eye;
   (c) performing, by a processor comprising a non-transient computer readable medium comprising processor-executable instructions, at least the following steps:
      (i) determining a first range of an ultrasonic transducer aperture relative to the at least one selected feature of the patient's eye;
      (ii) moving a position of at least one of an ultrasonic transducer and arcuate guide relative to the at least one selected feature of the patient's eye;
      (iii) determining a predetermined range of the at least one of an ultrasonic transducer and arcuate guide relative to the at least one selected feature of the patient's eye;
      (iv) executing, based on the set of scan meridians, a series of ultrasonic scans of the patient's eye; and
      (v) executing, based on the set of scan analysis instructions, at least one of a set of acoustic images for each selected scan meridian, a set of eye component thickness maps, and major dimensions of the selected eye components.

18. The method of claim 17, wherein step (i) comprises the sub-steps:
   (I1) performing a series of ultrasonic A-scans;
   (I2) determining an A-scan representation of the selected feature of the patient's eye; and (I3) setting a focal plane of the ultrasonic transducer aperture on the A-scan representation.

19. The method of claim 17, wherein step (ii) comprises the sub-steps:
(II1) executing a series of B-scans along the prime meridian;
(II2) determining from a selected B-scan whether or not the arcuate guide is centered laterally and automatically move the arcuate guide by applying the following rules:
(1) when the selected B-scan is horizontal, the arcuate guide is centered laterally; and
(2) when the selected B-scan is not horizontal, the arcuate guide is not centered and the processor causes automated lateral movement of the arcuate guide until the selected B-scan is horizontal;
(II3) determining from a selected B-scan whether or not the arcuate guide is centered vertically and automatically move the arcuate guide by applying the following rules:
(1) when the selected B-scan is not curved, the arcuate guide is centered vertically;
(2) when the selected B-scan is curved, the arcuate guide is not centered vertically and the processor causes automated vertical movement of the arcuate guide until the selected B-scan is uncurved; and
(II4) rotating the arcuate guide through an angle from the prime meridian to a second meridian; and
(II5) repeating steps (II1)-(II3) with respect to the second meridian and then returning the arcuate guide to the prime meridian.

20. The method of claim 17, wherein the selected feature is at least one of a cornea, a natural lens, an artificial lens, an iris, a retina, diseased ocular tissue, damaged ocular tissue and injured ocular tissue, and further comprising:
moving a fixation light to change a degree of focus of the patient's eye.

21. An ocular imaging method, comprising:
(a) receiving, from an operator, a selection of at least one feature of a patient's eye, a set of one or more scan meridians comprising at least one of a prime scan meridian and one or more secondary scan meridians, a set of scan movement instructions and a set of scan analysis instructions;
(b) determining, by a processor, an alignment of an ultrasonic transducer with an axis of a patient's eye;
(c) determining, by a processor, a centering of an ultrasonic transducer relative to the at least one selected feature of the patient's eye;
(d) determining, by a processor, a first focal range of an ultrasonic transducer aperture relative to the at least one selected feature of the patient's eye;
(e) moving, by a processor, a position of at least one of an ultrasonic transducer and arcuate guide relative to the at least one selected feature of the patient's eye to focus the transducer to within a first selected value;
(f) acquiring, by a processor, a B-scan of the cornea and determining a tilt and a curvature of one or more of the layers of the cornea;
(g) determining, by a processor, a lateral and a vertical adjustment to the at least one of an ultrasonic transducer and arcuate guide to reduce the tilt and curvature to below a selected value;
(h) altering, by a processor, a vertical and lateral position of at least one of an ultrasonic transducer and arcuate guide relative to the at least one selected feature of the patient's eye based on the adjustments determined in step (g);
(i) determining, by a processor, a location of a focal region of the at least one of an ultrasonic transducer and arcuate guide relative to the at least one selected feature of the patient's eye to locate the focal region of the transducer to within a second selected value which is closer to the at least one selected feature of the patient's eye than the first selected value;
(j) altering, by a processor, a position of at least one of an ultrasonic transducer and arcuate guide relative to the at least one selected feature of the patient's eye to locate the focal region of the transducer to within the second selected value;
(k) executing, based on the set of scan meridians and scan movement instructions, a series of ultrasonic scans of the patient's eye; and
(l) executing, based on the set of scan analysis instructions, at least one of a set of acoustic images for each selected scan meridian, a set of eye component thickness maps, and major dimensions of the selected eye components.

* * * * *